United States Patent
Schuchman et al.

(10) Patent No.: US 9,492,514 B2
(45) Date of Patent: Nov. 15, 2016

(54) CERAMIDE LEVELS IN THE TREATMENT AND PREVENTION OF INFECTIONS

(71) Applicants: ICAHN SCHOOL OF MEDICINE AT MOUNT SINAI, New York, NY (US); YEDA RESEARCH AND DEVELOPMENT CO. LTD. AT THE WEIZMANN INSTITUTE OF SCIENCE, Rehovot (IL); UNIVERSITAET DUISBURG-ESSEN, Essen (DE)

(72) Inventors: Edward H. Schuchman, Haworth, NJ (US); Erich Gulbins, Essen (DE); Anthony Futerman, Rehovot (IL); Yael Pewzner-Jung, Rehovot (IL)

(73) Assignees: Icahn School of Medicine at Mount Sinai, New York, NY (US); Universitaet Duisberg-Essen, Essen (DE); Yeda Research and Development Co. Ltd. at the Weizmann Institute of Science, Rehovot (IL)

( * ) Notice: Subject to any disclaimer, the term of this patent is extended or adjusted under 35 U.S.C. 154(b) by 0 days.

(21) Appl. No.: 14/404,881

(22) PCT Filed: May 31, 2013

(86) PCT No.: PCT/US2013/043608
§ 371 (c)(1),
(2) Date: Dec. 1, 2014

(87) PCT Pub. No.: WO2013/181530
PCT Pub. Date: Dec. 5, 2013

(65) Prior Publication Data
US 2015/0125439 A1 May 7, 2015

Related U.S. Application Data

(60) Provisional application No. 61/654,519, filed on Jun. 1, 2012.

(51) Int. Cl.
*A61K 38/50* (2006.01)
*A61K 9/00* (2006.01)
*A61K 9/12* (2006.01)
*A61K 45/06* (2006.01)

(52) U.S. Cl.
CPC ............ *A61K 38/50* (2013.01); *A61K 9/0073* (2013.01); *A61K 9/12* (2013.01); *A61K 45/06* (2013.01); *C12Y 305/01023* (2013.01); *A61K 9/0014* (2013.01); *A61K 9/0019* (2013.01)

(58) Field of Classification Search
None
See application file for complete search history.

(56) References Cited

U.S. PATENT DOCUMENTS

| | | |
|---|---|---|
| 3,966,555 A | 6/1976 | Arnaud et al. |
| 3,972,777 A | 8/1976 | Yamada et al. |
| 4,450,238 A | 5/1984 | Vitobello et al. |
| 4,837,028 A | 6/1989 | Allen |
| 5,019,369 A | 5/1991 | Presant et al. |
| 5,382,524 A | 1/1995 | Desnick et al. |
| 5,401,650 A | 3/1995 | Desnick et al. |
| 5,433,946 A | 7/1995 | Allen, Jr. et al. |
| 5,580,757 A | 12/1996 | Desnick et al. |
| 5,688,766 A | 11/1997 | Revis |
| 6,066,626 A | 5/2000 | Yew et al. |
| 6,258,581 B1 | 7/2001 | Okino et al. |
| 6,350,768 B1 | 2/2002 | Bohme et al. |
| 6,489,117 B2 | 12/2002 | Okino et al. |
| 6,537,785 B1 | 3/2003 | Canfield |
| 6,541,218 B1 | 4/2003 | Schuchman et al. |
| 6,730,297 B1 | 5/2004 | Davidson et al. |
| 6,767,741 B1 | 7/2004 | Epstein et al. |
| RE38,689 E | 1/2005 | Okino et al. |
| 6,858,383 B2 | 2/2005 | Sabbadini |
| 6,881,546 B2 | 4/2005 | Sabbadini |
| 6,884,435 B1 | 4/2005 | O'Hagan et al. |
| 7,018,628 B1 | 3/2006 | Sarkis et al. |

(Continued)

FOREIGN PATENT DOCUMENTS

| | | |
|---|---|---|
| JP | 2002/542195 A | 12/2002 |
| JP | 2003/516122 A | 5/2003 |
| JP | 2004/083465 A | 3/2004 |
| WO | WO 90/11353 | 10/1990 |
| WO | WO 00/62780 | 10/2000 |
| WO | WO 01/26678 A1 | 4/2001 |
| WO | WO 02/087510 A2 | 11/2002 |
| WO | WO 2004/057031 A2 | 7/2004 |
| WO | WO 2006/007560 A2 | 1/2006 |
| WO | WO 2006/113289 A2 | 10/2006 |

(Continued)

OTHER PUBLICATIONS

Park et al., Acid Ceramidase and human disease, Biochimica et Biophysica Acta 1758 (2006) 2133-2138.*
International Search Report and Written Opinion for corresponding International Application No. PCT/US2013/043608 (mailed Oct. 21, 2013).

(Continued)

*Primary Examiner* — Suzanne M Noakes
*Assistant Examiner* — Stephen Chong
(74) *Attorney, Agent, or Firm* — LeClairRyan, a Professional Corporation

(57) ABSTRACT

The present invention relates to a method for treating or preventing pathogenic infections in a subject having Cystic Fibrosis, COPD, and/or an open wound. This method involves selecting a subject having Cystic Fibrosis, COPD, and/or an open wound and administering to the selected subject a ceramidase under conditions effective to reduce ceramide and to treat or prevent the pathogenic infection. The method also involves the use of a ceramidase in combination with other drugs to reduce infection, reduce ceramide, or improve lung function in Cystic Fibrosis, COPD, and/or open wound patients.

18 Claims, 3 Drawing Sheets

(56) References Cited

U.S. PATENT DOCUMENTS

| | | | |
|---|---|---|---|
| 7,232,670 | B2 | 6/2007 | D'Azzo et al. |
| 7,273,756 | B2 | 9/2007 | Adkisson et al. |
| 7,927,587 | B2 | 4/2011 | Blazer et al. |
| 8,017,394 | B2 | 9/2011 | Adkisson, IV et al. |
| 2003/0087868 | A1 | 5/2003 | Yew et al. |
| 2003/0157086 | A1 | 8/2003 | Tilly et al. |
| 2003/0211604 | A1 | 11/2003 | Brown |
| 2003/0215435 | A1 | 11/2003 | Berent |
| 2004/0029779 | A1 | 2/2004 | Zhu et al. |
| 2004/0039046 | A1 | 2/2004 | Deigner |
| 2004/0172665 | A1 | 9/2004 | Reuser et al. |
| 2004/0204379 | A1 | 10/2004 | Cheng et al. |
| 2004/0242539 | A1 | 12/2004 | Fan et al. |
| 2004/0247603 | A1 | 12/2004 | Sabbadini |
| 2004/0248262 | A1 | 12/2004 | Koeberl et al. |
| 2005/0026823 | A1 | 2/2005 | Zankel et al. |
| 2005/0112640 | A1 | 5/2005 | Davidson et al. |
| 2006/0154252 | A1 | 7/2006 | Marguerie et al. |
| 2007/0009500 | A1 | 1/2007 | Blazar et al. |
| 2007/0162992 | A1 | 7/2007 | Burns |
| 2007/0184439 | A1 | 8/2007 | Guilford et al. |
| 2007/0292949 | A1 | 12/2007 | Duguay et al. |
| 2008/0045470 | A1 | 2/2008 | Bielawska et al. |
| 2008/0057590 | A1 | 3/2008 | Urdea et al. |
| 2008/0199450 | A1 | 8/2008 | Schuchman et al. |
| 2008/0248481 | A1 | 10/2008 | Rapko et al. |
| 2008/0292618 | A1 | 11/2008 | Weisbart |
| 2010/0068302 | A1 | 3/2010 | Ramirez De Molina et al. |
| 2010/0160253 | A1 | 6/2010 | Coombe et al. |
| 2010/0285139 | A1 | 11/2010 | Gulbins |
| 2011/0091439 | A1 | 4/2011 | Bernard et al. |
| 2011/0091442 | A1 | 4/2011 | Boyd et al. |
| 2014/0287015 | A1 | 9/2014 | Schuchman et al. |
| 2015/0132368 | A1 | 5/2015 | Muro Galindo et al. |

FOREIGN PATENT DOCUMENTS

| | | |
|---|---|---|
| WO | WO 2007/089734 A2 | 8/2007 |
| WO | WO 2007/095688 A1 | 8/2007 |
| WO | WO 2007/117996 A2 | 10/2007 |
| WO | 2007136635 A1 | 11/2007 |
| WO | WO 2008/086296 A2 | 7/2008 |
| WO | 2009155936 A1 | 12/2009 |
| WO | WO 2010/127355 A1 | 11/2010 |
| WO | WO 2011/025996 A2 | 3/2011 |
| WO | 2011066352 A1 | 6/2011 |
| WO | 2012051415 A2 | 4/2012 |
| WO | WO 2012/051415 A2 | 4/2012 |
| WO | WO 2012/154794 A2 | 11/2012 |
| WO | WO 2012/177778 A1 | 12/2012 |
| WO | 2013036875 A1 | 3/2013 |
| WO | 2013101276 A2 | 7/2013 |
| WO | WO 2013/181530 A1 | 12/2013 |
| WO | WO 2014/160390 A1 | 10/2014 |

OTHER PUBLICATIONS

Grassme et al., "CFTR-Dependent Susceptibility of the Cystic Fibrosis-Host to Pseudomonas aeruginosa," Int. J. Med. Microbiol. 300:578-583 (2010).

Teichgraber et al., "Ceramide Accumulation Mediates Inflammation, Cell Death and Infection Susceptibility in Cystic Fibrosis," Nat. Med. 14(4):382-391 and Supplementary Information (2008).

Achord et al., "Human beta-Glucuronidase: In Vivo Clearance and In vitro Uptake by a Glycoprotein Recognition System on Reticuloendothelial Cells," Cell 15(1):269-78 (1978).

Agnieszka et al., "Prenatal Diagnosis-Principles of Diagnostic Procedures and Genetic Counseling," Folia Histochemica et Cytobiologica 45:11-16 (2007).

Almenar-Queralt et al., "Apical Topography and Modulation of ICAM-1 Expression on Activated Endothelium," Am. J. Pathol. 147(5): 1278-88 (1995).

Auclair et al., "Intra-Articular Enzyme Administration for Joint Disease in Feline Mucopolysaccharidosis VI: Enzyme Dose and Interval," Pediatr. Res. 59(4):538-43 (2006).

Barton et al., "Therapeutic Response to Intravenous Infusions of Glucocerebrosidase in a Patient with Gaucher Disease," Proc. Natl. Acad. Sci. USA 87(5): 1913-6 (1990).

Bawab et al., "Ceramidases in the Regulation of Ceramide Levels and Function," Subcellular Biochemistry, vol. 36, Chapter 10, Phospholipid Metabolism in Apoptosis, Quinn et al., Eds., Kluwer Academic/Plenum Publishers, New York (2002).

Bazian, "Ultra Drug Orphan Drugs for Lysosomal Storage Disorders: A Guideline Comparison and Survey of International Current Practice," 1-70 (2009).

Becker et al., "Acid Sphingomyelinase Inhibitors Normalize Pulmonary Ceramide and Inflammation in Cystic Fibrosis," Am. J. Respir. Cell Mol. Biol. 42:716-24 (2010).

Berlin and Oliver, "Surface Functions During Mitosis," J. Cell. Biol. 85:660-671 (1980).

Bernardo et al., "Purification, Characterization, and Biosynthesis of Human Acid Ceramidase," J. Biol. Chem. 270(19): 11098-11102 (1995).

Bernstein et al., "Fabry Disease: Six Gene Rearrangements and an Exonic Point Mutation in the alpha-Galactosidase Gene," J. Clin. Invest. 83(4):1390-1399 (1989).

Beutler et al., "Purification and Properties of Human alpha-Galactosidases," J. Biol. Chem. 247(22):7195-7200 (1972).

Beutler, E., "Gaucher Disease: New Molecular Approaches to Diagnosis and Treatment," Science 256:794-799 (1992).

Bhowmick et al., "Effect of Flow on Endothelial Endocytosis of Nanocarriers Targeted to ICAM-1," J. Controlled Release 157(3):485-492 (2012).

Bielicki et al., "Advantages of Using Same Species Enzyme for Replacement Therapy in a Feline Model of Mucopolysaccharidosis Type VI," The Journal of Biological Chemistry 274(51):36335-36343 (1999).

Bielicki et al., "Recombinant Canine alpha-L-Fucosidase: Expression, Purification, and Characterization," Mol. Gen. Metabolism 69:24-32 (2000).

Bishop et al., "Affinity Purification of alpha-Galactosidase A From Human Spleen, Placenta, and Plasma With Elimination of Pyrogen Contamination. Properties of the Purified Splenic Enzyme Compared to other Forms," J. Biol. Chem. 256(3):1307-1316 (1981).

Bishop et al., "Enzyme Therapy XX: Further Evidence for the Differential In Vivo Fate of Human Splenic and Plasma . . . ", in Lysosomes and Lysosomal Storage Diseases, Eds. Callahan et al. Raven Press; 381-94 (1981).

Bishop et al., "Human alpha-Galactosidase A: Nucleotide Sequence of a cDNA Clone Encoding the Mature Enzyme," Proc. Natl. Acad. Sci. 83(13):4859-4863 (1986).

Bishop et al., "Human α-Galactosidase: Characterization and Eukaryotic Expression of the Full-Length cDNA and Structural Organization of the Gene" in Lipid Storage Disorders, Eds. Salvayre et al. Plenum Publishing Corp 809-822 (1988).

Bishop et al., "Molecular Cloning and Nucleotide Sequencing of a Complementary DNA Encoding Human Alpha Galactosidase A," Am. J. Hum. Genetics 37 (4 Suppl):A144 (1985).

Bishop et al., "Purification and Characterization of Human alpha-Galactosidase Isozymes: Comparison of Tissue and Plasma Forms and Evaluation of Purification Methods," Birth Defects Original Article Series; XVI(1): 17-32 (1980).

Bishop et al., "Structural Organization of the Human alpha-Galactosidase A Gene: Further Evidence for the Absence of a 3' Untranslated Region," Proc. Natl. Acad. Sci. 85(11):3903-3907 (1988).

Bodas et al., "Critical Modifier Role of Membrane-Cystic Fibrosis Transmembrane Conductance Regulator-Dependent Ceramide Signaling in Lung Injury and Emphysema," J. Immunol. 186:602-613 (2011).

Bonten et al., "Targeting Macrophages With Baculovirus-Produced Lysosomal Enzymes: Implications for Enzyme Replacement Therapy of the Glycoprotein Storage Disorder Galactosialidosis," FASEB J. 18(9):971-3 (Epub 2004).

(56) References Cited

OTHER PUBLICATIONS

Boose et al., "Conditional Intercellular Cohesion in a *Dictyostelium discoideum* Mutant Which is Temperature Sensitive for Correct Processing of Asparagine-Linked Oligosaccharides," *Glycobiology* 1(3):295-305 (1991).
Brady et al., "Enzyme Replacement Therapy: Conception, Chaos and Culmination." *Phil. Trans. R. Soc. London B Biol. Sci.* 358(1433):915-9 (2003).
Brady et al., "Modifying Exogenous Glucocerebrosidase for Effective Replacement Therapy in Gaucher Disease," *J. Inherit. Dis.* 17(4):510-9 (1994).
Brady et al., "Replacement Therapy for Inherited Enzyme Deficiency. Use of Purified Ceramidetrihexosidase in Fabry's Disease." *N. Engl. J. Med.* 289(1):9-14 (1973).
Broun et al., "Catalytic Plasticity of Fatty Acid Modification Enzymes Underlying Chemical Diversity of Plant Lipids," *Science* 282:1315-1317 (1998).
Cabrera-Salazar et al., "Gene Therapy for the Lysosomal Storage Disorders," *Curr. Opin. Mol. Ther.* 4(4):349-58 (2002).
Calhoun et al., "Fabry Disease: Isolation of a cDNA Clone Encoding Human Alpha-Galactosidase A," *Proc. Natl. Acad. Sci.* 82(21):7364-7368 (1985).
Callahan et al., "Alpha-N-Acetylgalactosaminidase: Isolation, Properties and Distribution of the Human Enzyme," *Biochemical Med.* 7(3):424-431 (1973).
Chavez et al., "Acid Ceramidase Overexpression Prevents the Inhibitory Effects of Saturated Fatty Acids in Insulin Signaling," *J. Biol. Chem.* 280(20):20148-53 (2006).
Chelikani et al., "Diversity of Structures and Properties Among Catalases," *Cell Mol. Life Sci.* 61:192-208 (2004).
Chica et al., "Semi-Rational Approaches to Engineering Enzyme Activity: Combining the Benefits of Directed Evolution and Rational Design," *Curr. Opi. Biotechnol.* 16:378-384 (2005).
Christofidou-Solomidou et al., "Vascular Immunotargeting of Glucose Oxidase to the Endothelial Antigens Induces Distinct Forms of Oxidant Acute Lung Injury: Targeting to Thrombomodulin, but not to PECAM-1, Causes Pulmonary Thrombosis and Neutrophil Transmigration," *Am. J. Pathol.* 160(3):1155-69 (2002).
Conner and Schmid, "Regulated Portals of Entry Into the Cell," *Nature* 422:37-44 (2003).
Coppola et al., "Construction of. Baculovirus Derivatives that Overproduce Human α-Galactosidase A," *J. Cell. Biochem. Suppl.* Abstract No. K306 13D:227-347 (1989).
D' Azzo, "Gene Transfer Strategies for Correction of Lysosomal Storage Disorders," *Acta Haematol.* 110(2-3):71-85 (2003).
Daly & Sands, "Gene Therapy for Lysosomal Storage Diseases," *Expert Opin. Invest. Drugs* 7(10):1673-82 (1998).
Dean et al., "Studies on Human Liver Alpha-Galactosidases. II. Purification and Enzymatic Properties of Alpha-Galactosidase B (alpha-N-acetylgalactosaminidase)," *J. Biol. Chem.* 254(20):10001-10005 (1979).
Dean et al., "The Identification of Alpha-Galactosidase B From Human Liver as an Alpha-N-Acetylgalactosaminidase," *Biochem. Biophys. Res. Commun.* 77(4): 1411-1417 (1977).
Desnick et al., "Enzyme Replacement and Enhancement Therapies: Lessons From Lysosomal Disorders," *Nature Rev. Genet.*; 3(12):954-66 (2002).
Desnick et al., "Enzyme Therapy in Fabry Disease: Differential In Vivo Plasma Clearance and Metabolic Effectiveness of Plasma and Splenic Alpha-Galactosidase A Isozymes," *Proc. Natl. Acad. Sci. USA* 76(10):5326-5330 (1979).
Desnick et al., "Enzyme therapy XVII: Metabolic and Immunologic Evaluation of Alpha-Galactosidase A Replacement in Fabry Disease," *Birth Defects Original Article Series*; XVI(1):393-413 (1980).
Desnick et al., "Fabry Disease: a-Galactosidase Deficiency; Schindler Disease: α-N-Acetylgalactosaminidase Deficiency." in *The Metabolic Basis of Inherited Disease*, eds. Scriver et al. McGraw Hill, NY; 70: 1751-96 (1989).
Desnick et al., "Fabry Disease: Molecular Diagnosis of Hemizygotes and Heterozygotes," *Enzyme* 38(1-4):54-64 (1987).
Desnick et al., "Schindler Disease: An Inherited Neuroaxonal Dystrophy Due to alpha-N-Acetylgalactosaminidase Deficiency," *J. Inher. Metab. Dis.* 13:549-559 (1990).
Devos et al., "Practical Limits of Function Prediction," *Proteins: Structure, Function, and Genetics* 41:98-107 (2000).
Dhami et al., "Mannose 6-phosphate Receptor-Mediated Uptake is Defective in Acid Sphingomyelinase-Deficient Macrophages: Implications for Niemann-Pick Disease Enzyme Replacement Therapy," *J. Biol. Chem.* 279(2): 1526-32 (2004).
Diamond et al., "Binding of the Integrin Mac-1 (CD11b/CD18) to the Third Immunoglobulin-Like Domain of ICAM-1 (CD54) and its Regulation by Glycosylation," *Cell* 65:961-71 (1991).
Eliyahu et al., "Acid Ceramidase Improves the Quality of Oocytes and Embryos and the Outcome of in Vitro Fertilization," *FASEB J.* 24:1229-38 (2010).
Eliyahu et al., "Acid Ceramidase is a Novel Factor Required for Early Embryo Survival," Abstract Presented in Mar. 2007.
Eliyahu et al., "Acid Ceramidase is a Novel Factor Required for Early Embryo Survival," *FASEB J.* 21:1403-09 (May 2007).
Eliyahu et al., "Anti-TNF-Alpha Therapy Enhances the Effects of Enzyme Replacement Therapy in Rats with Mucopolysaccharidosis Type VI," *PLOS ONE* 6(8):e22447 (2011).
Eliyahu et al., "Identification of Cystatin SA As a Novel Inhibitor of Acid Ceramidase," *J. Biol. Chem.* 286(41):35624-33 (2011).
Ellinwood et al., "Gene Therapy for Lysosomal Storage Diseases: The Lessons and Promise of Animal Models," *J. Gene Med.* 6(5):481-506 (2004).
Eng et al., "Safety and Efficacy of Recombinant Human alpha-Galactosidase A Replacement Therapy in Fabry's Disease," *N. Eng. J. Med.* 345(1):9-16 (2001).
Estruch et al., "Non-Viral, Integrin-Mediated Gene Transfer into Fibroblasts From Patients With Lysosomal Storage Diseases." in *J. Gene Med.* 3(5):488-97 (2001).
European Patent Application No. 08727393.4, Supplementary European Search Report (Sep. 9, 2010).
European Patent Office Communication and Examination Report for European Patent Application No. 08727393.4 (Dec. 4, 2014).
Extended European Search Report and Opinion for European Patent Application No. 12830086.0 (dated Jul. 13, 2015).
Extended European Search Report for European Patent Application No. 12803458.4 (dated Mar. 20, 2015).
Farkas et al., "The Recycling of Apolipoprotein E and its Amino-Terminal 22 kDa Fragment: Evidence of Multiple Redundant Pathways," *J. Lipid Res.* 45:1546-1554 (2004).
Fawcett, "Surface Specializations of Absorbing Cells," *J. Histochem. Cytochem.* 13(2):75-91 (1965).
Ferlinz et al., "Functional Characterization of the N-Glycosylation Sites of Human Acid Sphingomyelinase by Site-Directed Mutagenesis," *Eur. J. Biochem.* 243:511-517 (1997).
Ferlinz et al., "Occurrence of Two Molecular Forms of Human Acid Sphingomyelinase," *Biochem. J.* 301:855-862 (1994).
First Office Action and English Translation for Chinese Patent Application No. 201280037341 5 (mailed Dec. 3, 2014).
Fox et al., "Circulating Sphingolipid Biomarkers in Models of Type 1 Diabetes," *Journal of Lipid Research*, 30 pp., retrieved from www.jlr.org on Jan. 6, 2011.
Friedman et al., "A Comparison of the Pharmacological Properties of Carbohydrate Remodeled Recombinant and Placental-Derived beta-Glucocerebrosidase: Implications for Clinical Efficacy in Treatment of Gaucher Disease," *Blood* 93(9):2807-16 (1999).
Furbish et al., "Uptake and Distribution of Placental Glucocerebrosidase in Rat Hepatic Cells and Effects of Sequential Deglycosylation," *Biochem. Biophys. Acta.* 673(4):425-34 (1981).
Gao et al., "Delivery of a Retroviral Vector Expressing Human beta-Glucuronidase to the Liver and Spleen Decreases Lysosomal Storage in Mucopolysaccharidosis VII Mice," *Mol. Ther.* 2(2):233-44 (2000).
Garman & Garboczi, "The Molecular Defect Leading to Fabry Disease: Structure of Human α-Galactosidase", *J. Mol. Biol.* 337(2):319-335 (2004).

(56) References Cited

OTHER PUBLICATIONS

Garman et al., "The 1.9 A Structure of α-N-Acetylgalactosaminidase", *Structure* 10(3):425-434 (2002).
Gilbert et al., "Sphingomyelinase Decreases Type II Collagen Expression in Bovine Articular Cartilage Chondrocytes via the ERK Signaling Pathway," *Arthritis & Rheumatism* 58(1):209-220 (2008).
Gole et al. "Plasma Proteins Modified by Tyrosine Nitration in Acute Respiratory Distress Syndrome," *Am. J. Physiol. Lung Cell Mol. Physiol.* 278(5):L961-967 (2000).
Grabowski et al., "Enzyme Therapy for Lysosomal Storage Disease: Principles, Practice, and Prospects." *Aunu. Rev. Genomics Hum. Genet.*; 4:403-36 (2003).
Grabowski et al., "Enzyme Therapy in Type 1 Gaucher Disease: Comparative Efficacy of Mannose-Terminated Glucocerebrosidase from Natural and Recombinant Sources," *Ann. Intern. Med.* 122:33-39 (1995).
Hanzopoulos & Calhoun, "Expression of the Human alpha-Galactosidase A in *Escherichia coli* K-12," *Gene (Amst.)* 57(2-3):159-169 (1987).
Harmatz et al., "Enzyme Replacement Therapy in Mucopolysaccharidosis VI (Maroteaux-Lamy Syndrome)," *J. Pediatr.* 144:574-80 (2004).
Hasholt & Sorenson, "Lysosomal Alpha-Galactosidase in Endothelial Cell Cultures Established From a Fabry Hemizygous and Normal Umbilical Veins," *Human Genet.* 72(1):72-76 (1986).
Haskins et al., "Bone Marrow Transplantation Therapy for Metabolic Disease: Animal Models as Predictors of Success and in Utero Approaches," *Bone Marrow Transplant* 18(Suppl. 3): S25-S27 (1996).
He et al., "Characterization of Human Acid Sphingomyelinase pPurified From the Media of Overexpressing Chinese Hamster Ovary Cells," *Biochim. Biophys. Acta.* 1432(2):251-64 (1999).
He et al., "Deregulation of Sphingolipid Metabolism in Alzheimer's Disease," *Neurobiology of Aging* 31(3):398-408 (2010).
He et al., "Purification and Characterization of Recombinant, Human Acid Ceramidase. Catalytic Reactions and Interactions With Acid Sphingomyelinase," *J. Biol. Chem.* 278(35):32978-86 (2003).
Hers et al., "Alpha-Glucosidase Deficiency in Generalized Glycogenstorage Gisease (Pompe's Gisease)," *Biochem. J.* 86:11-16 (Jan. 1963).
Hlavacek et al., "Steric Effects on Multivalent Ligand-Receptor Binding: Exclusion of Ligand Sites by Bound Cell Surface Receptors," *Biophysical J.* 76:3031-3043 (1999).
Hoogerbrugge et al., "Effect of Bone Marrow Transplantation on Enzyme Levels and Clinical Course in the Neurologically Affected Twitcher Mouse," *J. Clin. Invest.* 81(6): 1790-4 (Jun. 1988).
Huang et al., "A Comparison of the Signal Pathways Between the TNFalpha- and Oridonin-Induced Murine L929 Fibrosarcoma Cell Death," *Acta Med. Okayama* 59(6):261-70 (2005).
Huang et al., "Elevation of the Level and Activity of Acid Ceramidase in Alzheimer's Disease Brain," *Europ. J. Neurosci.* 20:3489-3497 (2004).
International Preliminary Report on Patentability for PCT/US2008/050418 (mailed Jul. 16, 2009).
International Search Report and Written Opinion for PCT/US2008/050418 (mailed Oct. 8, 2008).
International Search Report and Written Opinion for International Application No. PCT/US05/23529 (mailed Aug. 2, 2006).
International Search Report and Written Opinion for International Application No. PCT/US2014/026481 (mailed Aug. 11, 2014).
International Search Report and Written Opinion for PCT Application No. PCT/US2012/043369 (mailed Aug. 31, 2012).
International Search Report and Written Opinion for PCT/US10/33422 (mailed Jun. 29, 2010).
International Search Report and Written Opinion for PCT/US11/56147 (mailed Apr. 26, 2012).
International Search Report and Written Opinion for PCT/US2012/031847 (dated Jul. 22, 2013).
International Search Report and Written Opinion for PCT/US2012/054316 (mailed Dec. 20, 2012).

Ioannou et al., "Overexpression and Characterization of Human alpha-Galactosidase," in *Inborn Errors of Metabolism, 5th International Congress*, Abstract No. OC4.3, Pacific Grove, CA (Jun. 1-5, 1990).
Ioannou et al., "Fabry Disease: Preclinical Studies Demonstrate the Effectiveness of alpha-Galactosidase A Replacement in Enzyme-Deficient Mice," *Am J. Hum. Genet.* 68:14-25 (2001).
Isemura et al., "Characterization and Amino Acid Sequence of New Acidic Cysteine Proteinase Inhibitor (Cystatin SA) Structurally Closely Related to Cystatin S, From Human Whole Saliva," *J. Biochem.* 102(4):693-704 (1987).
Jan et al., "Sindbis Virus Entry Into Cells Triggers Apoptosis by Activating Sphingomyelinase," *J. Virol.* 74(14):6425-32 (2000).
Jin et al., "Ex Vivo Gene Therapy Using Bone Marrow-Derived Cells: Combined Effects of Intracerebral and Intravenous Transplantation in a Mouse Model of Niemann-Pick Disease," *Mol. Ther.* 8(6):876-85 (2003).
Jin et al., "Intracerebral Transplantation of Mesenchymal Stem Cells Into Acid Sphingomyelinase-Deficient Mice Delays the Onset of Neurological Abnormalities and Extends Their Life Span." *J. Clin. Invest.* 109(9):1183-91 (2002).
Kakkis et al., "Long-Term and High-Dose Trials of Enzyme Replacement Therapy in the Canine Model of Mucopolysaccharidosis I," *Biochem. Mol. Med.* 58:156-67 (1996).
Kaplan et al., "Phosphohexosyl Components of a Lysosomal Enzyme are Recognized by Pinocytosis Receptors on Human Fibroblasts," *Proc. Natl. Acad. Sci. USA*; 74(5):2026-30 (1977).
Kato et al., "Cystatin SA, A Cysteine Proteinase Inhibitor, Induces Interferon-Gamma Expression in CD4-Positive T Cells," *Biol. Chem.* 385(5):419-22 (2004).
Kishida et al., "Docosahexaenoic Acid Enrichment Can Reduce L929 Cell Necrosis Induced by Tumor Necrosis Factor," *Biochim. Biophys. Acta* 1761:454-62 (2006).
Kisselev, L., "Polypeptide Release Factors in Prokaryotes and Eurkaryotes: Same Function, Different Structure," *Structure* 10:8-9 (2002).
Klabunde et al., "Mechanism of FE(III)-Zn(II) Purple Acid Phosphatase Based on Crystal Structures," *J. Mol. Biol.* 259:737-748 (1996).
Kölzer et al., "Functional Characterization of the Postulated Intramolecular Sphingolipid Activator Protein Domain of Human Acid Sphingomyelinase," *Biol. Chem.* 385:1193-1195 (2004).
Kornfeld et al., "Lysosomal Enzyme Targeting," *Biochem. Soc. Trans.* 18(3):367-74 (1990).
Kornfeld et al., "Trafficking of Lysosomal Enzymes," *FASEB J.* 1(6):462-468 (1987).
Kornfeld et al., "Steps in the Phosphorylation of the High Mannose Oligosaccharides of Lysosomal Enzymes," *CIBA Found. Symp.*; (92):138-56 (1982).
Kornreich et al., "Alpha-Galactosidase A Gene Rearrangements Causing Fabry Disease. Identification of Short Direct Repeats at Breakpoints in an Alu-Rich Gene," *J. Biol. Chem.* 265(16): 9319-9326 (1990).
Kornreich et al., "Nucleotide Sequence of the Human Alpha-Galactosidase A Gene," *Nuc. Acids. Res.* 17(8):3301-3302 (1989).
Kozower et al., "Immunotargeting of Catalase to the Pulmonary Endothelium Alleviates Oxidative Stress and Reduces Acute Lung Transplantation Injury," *Nat. Biotechnol.* 21(4):392-8 (2003).
Krivit et al., "State of the Art Review. Bone Marrow Transplantation Treatment for Storage Diseases.Keystone," *Bone Marrow Transplant* 10(Suppl. 1): 87-96 (1992).
Kusiak et al., "Purification and Properties of the Two Major Isozymes of Alpha-Galactosidase From Human Placenta," *J. Biol. Chem.* 253(1): 184-190 (1978).
Lansmann et al., "Human Acid Sphingomyelinase—Assignment of the Disulfide Bond Pattern," *Eur. J. Biochem.* 270:1076-1088 (2003).
Le Roy et al., "Clathrin-and non-Clathrin Mediated Endocytic Regulation of Cell Signalling," *Nature* 6:112-126 (2005).
Lebowitz et al., "Glycosylation-Independent Targeting Enhances Enzyme Delivery to Lysosomes and Decreases Storage in Mucopolysaccharidosis Type VII Mice," *Proc. Natl. Acad. Sci. USA* 101(9):3083-8 (2004).

(56) References Cited

OTHER PUBLICATIONS

Leimig et al., "Functional Amelioration of Murine Galactosialidosis by Genetically Modified Bone Marrow Hematopoietic Progenitor Cells," *Blood* 99(9):3169-78 (2002).
Lemansky et al., "Synthesis and Processing of Alpha-Galactosidase A in Human Fibroblasts. Evidence for Different Mutations in Fabry Disease," *J. Biol. Chem.* 262(5):2062-2065 (1987).
Li et al., "Insertional Mutagenesis of the Mouse Acid Ceramidase Gene Leads to Early Embryonic Lethality in Homozygotes and Progressive Lipid Storage Disease in Heterozygotes," *Genomics* 79(2):218-24 (2002).
Lin et al., "*Caenorhabditis elegans* Contains Two Distinct Acid Sphingomyelinases," *J. Biol. Chem.* 273(23): 14374-14379 (1998).
Liu et al., "Acid Ceramidase Upregulation in Prostate Cancer: Role in Tumor Development and Implications for Therapy," *Expert Opinions in Therapeutic Targets* 13(12):1449-1458 (2009).
Macrae et al., "Ceramide Inhibition of Chondrocyte Proliferation and Bone Growth is IGF-I Independent," *Journal of Endocrinology* 191:369-377 (2006).
Malatack et al., "The Status of Hematopoietic Stem Cell Transplantation in Lysosomal Storage Disease," *Pediatr. Neurol.* 29(5):391-403 (2003).
Mao et al., "Cloning and Characterization of a Novel Human Ceramidase," *J. Biol. Chem.* 276(28):26577-26588 (2001).
Marquass et al., "Matrix-Associated Implantation of Predifferentiated Mesenchymal Stem Cells Versus Articular Chondrocytes," In Vivo Results of Cartilage Repair After 1 Year, *The American Journal of Sports Medicine* 39(7):1401-1412 (2011).
Medline Plus Online Dictionary; Definition for "embryo".
Meikle et al., "Prevalence of Lysosomal Storage Disorders." *JAMA* 281(3): 249-54 (1999).
Mielke et al., "Alterations of the Sphingolipid Pathway in Alzheimer's Disease: New Biomarkers and Treatment Targets?," *Neuromol. Med.* 12:331-340 (2010).
Mintzer et al., "A Novel High-Throughput Screening Format to Identify Inhibitors of Secreted Acid Sphingomyelinase," *J. Biomol. Screen* 10(3):225-34 (2005).
Miranda et al., "Biochemical, Pathological, and Clinical Response to Transplantation of Normal Bone Marrow Cells Into Acid Sphingomyelinase-Deficient Mice," *Transplantation* 65(7):884-92 (1998).
Miranda et al., "Bone Marrow Transplantation in Acid Sphingomyelinase-Deficient Mice: Engraftment and Cell Migration Into the Brain as a Function of Radiation, Age, and Phenotype," *Blood* 90(1):444-52 (1997).
Miranda et al., "Hematopoietic Stem Cell Gene Therapy Leads to Marked Visceral Organ Improvements and a Delayed Onset of Neurological Abnormalities in the Acid Sphingomyelinase Deficient Mouse Model of Niemann—Pick Disease," *Gene Ther.* 7:1768-76 (2000).
Miranda et al., "Infusion of Recombinant Human Acid Sphingomyelinase into Niemann-Pick Disease Mice Leads to Visceral, but Not Neurological, Correction of the Pathophysiology," *FASEB J.* 14:1988-95 (2000).
Mistry et al., "Therapeutic Delivery of Proteins to Macrophages: Implications for Treatment of Gaucher's Disease." *Lancet* 348(9041):1555-9 (1996).
Monick et al., "Cooperative Prosurvival Activity by ERK and Akt in Human Alveolar Macrophages is Dependent on High Levels of Acid Ceramidase Activity," *J. Immunol.* 173:123-35 (2004).
Morita et al., "Oocyte Apoptosis Is Suppressed by Disruption of the Acid Sphingomyelinase Gene or by Sphingosine-1-Phosphate Therapy," *Nat. Med.* 6(10):1109-14 (2000).
Murciano et al., "ICAM-Directed Vascular Immunotargeting of Antithrombotic Agents to the Endothelial Luminal Surface," *Blood* 101(10):3977-84 (2003).
Muro et al., "A Novel Endocytic Pathway Induced by Clustering Endothelial ICAM-1 or PECAM-1." *J. Cell Sci.* 116(Pt 8):1599-609 (2003).
Muro et al., "Endothelial Endocytic Pathways: Gates for Vascular Drug Delivery," *Curr. Vasc. Pharmacol.* 2(3 ):281-99 (2004).
Muro et al., "ICAM-1 Recycling in Endothelial Cells: A Novel Pathway for Sustained Intracellular Delivery and Prolonged Effects of Drugs," *Blood* 105(2):650-8 (2005).
Muro et al., "Slow Intracellular Trafficking of Catalase Nanoparticles Targeted to ICAM-1 Protects Endothelial Cells From Oxidative Stress," *Am. J. Physiol. Cell Physiol.* 285(5):C1339-47 (2003).
Murray, "Lectin-Specific Targeting of Lysosomal Enzymes to Reticuloendothelial Cells," *Meth. Enzymol.* 149:25-42 (1987).
Naslavsky et al., "Characterization of a Nonclathrin Endocytic Pathway: Membrane Cargo and Lipid Requirements," *Mol. Biol. Cell.* 15:3542-3552 (2004).
Nejadnik et al., "Autologous Bone Marrow-Derived Mesenchymal Stem Cells Versus Autologous Chondrocyte Implantation: An Observational Cohort Study," *The American Journal of Sports Medicine* 38(6):1110-1116 (2010).
Newman et al., "The Biology of PECAM-1," *J. Clin. Invest.* 99(1):3-8 (1997).
Newrzella et al., "Functional Analysis of the Glycosylation of Murine Acid Sphingomyelinase," *J. Biol. Chem.* 271(50):32089-32095 (1996).
Newrzella et al., "Molecular Cloning of the Acid Sphingomyelinase of the Mouse and the Organization and Complete Nucleotide Sequence of the Gene," *Biol. Chem. Hoppe-Seyler* 373:1233-1238 (1992).
Nichols et al., "Endocytosis Without Clathrin Coats," *TRENDS in Cell Biol.* 11(10):406-412 (2001).
Office Action for Canadian Patent Application No. 2,674,849 (dated Feb. 4, 2015).
Office Action for European Application No. 12803458.4 (dated Feb. 8, 2016).
Okino et al., "The Reverse Activity of Human Acid Ceramidase," *J. Biol. Chem.* 278(32):29948-53 (2003).
Pandey et al., "Recent Advances in the Immunology of Ceramide," *Exp. Mol. Pathol.* 82:298-309 (2007) (E-pub Oct. 12, 2006).
Park et al., "Ceramide, A Crucial Functional Lipid and Its Metabolic Regulation by Acid Ceramidase," *Food Science & Biotechnology* 19(4):859-864 (2010).
Partial Supplementary European Search Report for European Patent Application No. 12830086.0 (dated Mar. 5, 2015).
Partial Supplementary European Search Report for European Patent Application No. 12803458.4 (dated Dec. 1, 2014).
Pasqualotto et al., "Effect of Oxidative Stress in Follicular Fluid on the Outcome of Assisted Reproductive Procedures," *Fertility and Sterility* 81(4):973-76 (2004).
Patrizio et al., "Molecular Methods for Selection of the Ideal Oocyte," *Reproductive BioMedicine Online* 15(3):346-53 (2007).
Perez et al., "A Central Role for Ceramide in the Age-Related Acceleration of Apoptosis in the Female Germline," *FASEB J.* 19(7):860-2 (2005).
Pittis et al., "Acid Sphingomyelinase Identification of Nine Novel Mutations Among Italian Niemann Pick Type B Patients and Characterization of In Vivo Functional In-Frame Start Codon," *Human Mutation, Mutation in Brief* #734 p. 1-7 (2004).
Ponting et al., "Acid sphingomyelinase possesses a domain homologous to its activator proteins: saposins Band D," *Protein Science* 3:359-361 (1994).
Pratico et al., "Localization of Distinct F2-Isoprostanes in Human Atherosclerotic Lesions." *J. Clin. Invest.* 100(8):2028-34 (1997).
Prince et al., "Lipoprotein Receptor Binding, Cellular Uptake, and Lysosomal Delivery of Fusions Between the Receptor-Associated Protein (RAP) and Alpha-L-Iduronidase or Acid Alpha-Glucosidase," *J. Biol. Chem.* 279(33):35037-46 (2004).
Qui et al., "Activation of Human acid Sphingomyelinase Through Modification or Deletion of C-Terminal Cysteine," *J. Biol. Chem.* 278(35):32744-32752 (2003).
Quinn et al., "A Genomic Clone Containing the Promoter for the Gene Encoding the Human Lysosomal Enzyme, Alpha-Galactosidase A," *Gene (Amst.).* 58(2-3): 177-188 (1987).

(56) References Cited

OTHER PUBLICATIONS

Quintern et al., "Acid Sphingomyelinase From Human Urine: Purification and Characterization," *Biochimica et Biophysica Acta.* 922:323-336 (1987).
Ramsubir et al., "In Vivo Delivery of Human Acid Ceramidase Via Cord Blood Transplantation and Direct Injection of Lentivirus as Novel Treatment Approaches for Farber Disease," *Molecular Genetics and Metabolism* 95:133-141 (2008).
Rienzi et al., "Predictive Value of Oocyte Morphology in Human IVF: A Systematic Review of the Literature," *Hum. Reprod Update* 17(1):33-45 (2011).
Romiti et al., "Neutral/Alkaline and Acid Ceramidase Activities Are Actively Released by Murine Endothelial Cells," *Biochem. Biophys. Res. Comm.* 275:746-51 (2000).
Roudebush et al, "Embryonic Platelet-Activating Factor: An Indicator of Embryo Viability," *Hum. Reprod.* 17(5):1306-10 (2002).
Rousseau et al., "Utilization of Membranous Lipid Substrates by Membranous Enzymes: Activation of the Latent Sphingomyelinase of Hen Erythrocyte Membrane," *Arch. Biochern. Biophys.* 244(2):838-45 (1986).
Sands et al., "Biodistribution, Kinetics, and Efficacy of Highly Phosphorylated and Non-Phosphorylated Beta-Glucuronidase in the Murine Model of Mucopolysaccharidosis VII," *J. Biol. Chem.* 276(46):43160-5 (2001).
Schindler et al., "Neuroaxonal Dystrophy Due to Lysosomal Alpha-N-Acetylgalactosaminidase Deficiency," *New Eng. J. Med.* 320(26):1735-1740 (1989).
Schram et al., "The Identity of Alpha-Galactosidase B From Human Liver," *Biochimica et Biophysica Acta.* 482(1):138-144 (1977).
Schuchman et al., "Human Acid Sphingomyelinase Isolation, Nucleotide Sequence and Expression of the Full-Length and Alternatively Spliced cDNAs," *J. Biol. Chem.* 266(13):8531-8539 (1991).
Schuchman et al., "A Novel Use for Acid Ceramidase in Cell-Based Therapies for Degenerative Joint Diseases, Including the Mucopolysaccharidoses," *Molecular Genetics and Metabolism* 105:S56 (2012) (abstract only).
Schuchman et al., "Pentosan Polysulfate: A Novel Therapy for the Mucopolysaccharidoses," *PLOS ONE* 8(1):e54459.
Scriver et al., Part 16: Lysosomal Disorders in: The Metabolic and Molecular Bases of Inherited Disease, 8th ed., McGraw-Hill (2000).
Second Office Action and English Translation for Chinese Patent Application No. 201280037341 5 (mailed Nov. 3, 2015).
Seelan et al., "Human Acid Ceramidase is Overexpressed but Not Mutated in Prostate Cancer," *Genes Chromosomes & Cancer* 29:137 (2000).
Ségui et al., "Stress-Induced Apoptosis Is Not Mediated by Endolysosomal Ceramide," *FASEB J.* 14:36-47 (2000).
Seli et al., "Noninvasive Metabolomic Profiling of Embryo Culture Media Using Proton Nuclear Magnetic Resonance Correlates With Reproductive Potential of Embryos in Women Undergoing in vitro fertilization," *Fertil. Steril.* 90:2183-89 (2008).
Sen et al., "Developments in Directed Evolution for Improving Enzyme Functions," *Appl. Biochem. Biotechnol.* 143:212-223 (2007).
Shtraizent et al., "Autoproteolytic Cleavage and Activation of Human Acid Ceramidase," *J. Biol. Chem.* 283(17):11253-9 (2008).
Simonaro et al., "Acid Ceramidase Improves the Chondrogenic Phenotype of Primary and Mesenchymal Stem Cell-Derived Chondrocytes: Implications for Cartilage Repair," *Osteoarthritis and Cartilage* 19(S1):S114-S115 (2011).
Simonaro et al., "Acid Ceramidase Maintains the Chondrogenic Phenotype of Expanded Primary Chondrocytes and Improves the Chondrogenic Differentiation of Bone Marrow-Derived Mesenchymal Stem Cells," *PLOS One* 8(4):e62715 (2013).
Simonaro et al., "Involvement of the Toll-like Receptor 4 Pathway and Use of TNF-alpha Antagonists for Treatment of the Mucopolysaccharidoses," *PNAS* 107(1):222-227 (2010).

Springer et al., "Traffic Signals for Lymphocyte Recirculation and Leukocyte Emigration: The Multistep Paradigm," *Cell* 76(2):301-14 (1994).
Stahl et al., "Evidence for Receptor-Mediated Binding of Glycoproteins, Glycoconjugates, and Lysosomal Glycosidases by Alveolar Macrophages," *Proc. Natl. Acad. Sci. USA* 75(3):1399-403 (1978).
Strelow et al., "Overexpression of Acid Ceramidase Protects from Tumor Necrosis Factor-Induced Cell Death," *J. Exp. Med.* 192(5):601-11 (2000).
Supplementary European Search Report for European Patent Application No. 13797635.3 (dated Jan. 22, 2016).
Sweeley et al., "Post-Translational Processing Reactions Involved in the Biosynthesis of Lysosomal Alpha-N-Acetylgalactosaminidase in Cultured Human Fibroblasts," *Archives of Biochem & Biophys.* 233(1):158-65 (1983).
Tang et al., "Identification of PECAM-1 in Solid Tumor Cells and Its Potential Involvement in Tumor Cell Adhesion to Endothelium," *J. Biol. Chem.* 268(30):22883-22894 (1993).
Taylor et al., "Decreased Lysosomal Storage in the Adult MPS VII Mouse Brain in the Vicinity of Grafts of Retroviral Vector-Corrected Fibroblasts Secreting High Levels of Beta-Glucuronidase," *Nature Med.* 3(7): 771-74 (1997).
Thon et al., "The Murine TRAIL Receptor Signals Caspase-Independent Cell Death Through Ceramide," *Experimental Cell Research* 312:3808-21 (2006).
Tsuji et al., "Molecular Cloning of a Full-Length cDNA for Human Alpha-N-Acetylgalactosaminidase (alpha-galactosidase B)," *Biochern. Biophys. Res. Commun.* 163(3):1498-1504 (1989).
Tsuji et al. "Signal Sequence and DNA-Mediated Expression of Human Lysosomal Alpha-Galactosidase A," *Eur. J. Biochem.* 165(2):275-280 (1987).
UniProt_D7BW40 (last modified Aug. 10, 2010).
UniProt_Q19784 ( last modified Sep. 11, 2007).
UniProt_Q8YUN7 (last modified Mar. 1, 2002).
Vanier et al., "Niemann-Pick Diseases," Handbook of Clinical Neurology, 113(3rd series):1717-1721 (2013).
Vellodi et al., "Bone Marrow Transplantation for Mucopolysaccharidosis Type I: Experience of Two British Centres," *Arch. Dis. Child.* 76(2):92-99 (1997).
Voraberger et al., "Cloning of the Human Gene for Intercellular Adhesion Molecule 1 and Analysis of its 5 '-Regulatory Region," *J. Immunol.* 147(8):2777-2786 (1991).
Waheed et al., "Human Lysosomal Acid Phosphatase is Transported as a Transmembrane Protein to Lysosomes in Transfected Baby Hamster Kidney Cells," *EMBO J.* 7(8):2351-8 (1988).
Walia et al., "Autologous Transplantation of Lentivector/Acid Ceramidase-Transduced Hematopoietic Cells in Nonhuman Primates," *Human Gene Therapy* 22:679-687 (2011).
Wang et al., "Human Alpha-N -Acetylgalactosaminidase-Molecular Cloning, Nucleotide Sequence, and Expression of a Full-Length cDNA. Homology with Human Alpha-Galactosidase A Suggests Evolution From a Common Ancestral Gene," *J. Biol. Chem.* 265(35):21859-21866 (1990).
Wang et al., "Molecular Genetics of PKU in Orientals," *Am J. Hum. Genet.* 45 (4 Suppl) A228 (1989).
Wang et al., "Schindler Disease Biochemical and Molecular Characterization of a New Neuroaxonal Dystrophy Due to Alpha-n. Acetylgalactosaminidase Deficiency," *Am. J. Hum. Genet.* 43 (3 Suppl):A99 (1988).
Wang et al., "Schindler Disease: The Molecular Lesion in the Alpha-N-Acetylgalactosaminidase Gene That Causes an Infantile Neuroaxonal Dystrophy," *J. Clin. Invest.* 86(5):1752-1756 (1990).
Weinreb et al., "Effectiveness of Enzyme Replacement Therapy in 1028 Patients with Type 1 Gaucher Disease After 2 to 5 Years of Treatment: A Report from the Gaucher Registry," *Am. J. Med.* 113:112-19 (2002).
Weinstein et al., "Primary Structure of Beta-Galactoside Alpha 2,6-Sialyltransferase. Conversion of Membrane-Bound Enzyme to Soluble Forms by Cleavage of the NH2-Terminal Signal Anchor," *J. Biol. Chem.* 262(36):17735-43 (1987).
Whisstock et al., "Prediction of Protein Function from Protein Sequence," *Q. Rev. Biophysics* 36(3):307-340 (2003).

(56) References Cited

OTHER PUBLICATIONS

Wiewrodt et al., "Size-Dependent Intracellular Immunotargeting of Therapeutic Cargoes Into Endothelial Cells," *Blood* 99(3):912-22 (2002).
Wishart et al., "A Single Mutation Converts a Novel Phosphotyrosine Binding Domain Into a Dual-Specificity Phosphatase," *J. Biol. Chem.* 270(45):26782-26785 (1995).
Witkowski et al., "Conversion of b-ketoacyl Synthase to a Malonyl Decarboxylase by Replacement of the Active Cysteine With Glutamine," *Biochemistry* 38:11643-11650 (1999).
Witsenburg et al., "Cumulative Live Birth Rates in Cohorts of Patients Treated With in Vitro Fertilization or Intracytoplasmic Sperm Injection," *Fertil. Steril.* 84(1):99-107 (2005).
Xu et al., "Golgi Alkaline Ceramidase Regulates Cell Proliferation and Survival by Controlling Levels of Sphingosine and SIP," *The FASEB Journal* 20:1813-25 (2006).
Yamauchi et al., "Molecular Cloning of Two Species of cDNAs for Human Alpha-N-Acetylgalactosaminidase and Expression in Mammalian Cells," *Biochem. Biophys. Res. Commun.* 170(1):231-37 (1990).
Yeyati et al., "Fluorescence-Based Selection of Retrovirally Transduced Cells in the Absence of a Marker Gene: Direct Selection of Transduced Type B Niemann-Pick Disease Cells and Evidence for Bystander Correction," *Hum. Gene Ther.* 6(8):975-83 (1995).
Young et al., "Sphingolipids: Regulators of Crosstalk Between Apoptosis and Autophagy," *J. Lipid. Res.* 54:5-19 (2013).
Zhang et al., "Delivery of Beta-Galactosidase to Mouse Brain Via the Blood-Brain Barrier Transferrin Receptor," *J. Pharmacol. Exp. Ther.* 313 (3): 1075-81 (2005).
Zhu et al., "Dexamethasone-Mediated up-Regulation of the Mannose Receptor Improves the Delivery of Recombinant Glucocerebrosidase to Gaucher Macrophages." *J. Pharmacol. Exp. Ther.* 308(2):705-11 (2004).
Office Action for European Application No. 12803458.4 (Feb. 8, 2016).
Grassmé et al., "Rhinoviruses Infect Human Epithelial Cells via Ceramide-Enriched Membrane Platforms," J. of Biological Chemistry 280(28)(Issue of Jul. 15):26256-26262 (2005).
Gassert et al., "Induction of Membrane Ceramides: A Novel Strategy to Interfere with T Lymphocyte Cytoskeletal Reorganization in Viral Immunosuppression," PLoS Pathogens 5(10):1-11 (2009).
Gulbins et al., "Ceramide, Membrane Rafts and Infections," J. Mol. Med. 82:357-363 (2004).
Simons et al., "Cholesterol, Lipid Rafts, and Disease," J. of Clinical Investigation 110(5):597-603 (2002).
Becker et al., "Ceramide in Pseudomonas aeruginosa Infections and Cystic Fibrosis," Cell Physiol. Biochem. 26:57-66 (2010).
Esen et al., "Mechanisms of *Staphylococcus aureus* Induced Apoptosis of Human Endothelial Cells," Apoptosis 6 (6):431-439 (2001).
Grassmé et al., "Acidic Sphingomyelinase Mediates Entry of N. gonorrhoeae into Nonphagocytic Cells," Cell 91:605-615 (1997).
Grassmé et al., "Host Defense Against *Pseudomonas aeruginosa* Requires Cermaide-Rich Membrane Rafts," Nature Medicine 9(3):322-330 (2003).
Dreschers et al., "Infections with Human Rhinovirus Induce the Formation of Distinct Functional Membrane Domains," Cell Physiol. Biochem. 20:241-254 (2007).
Juengst, E.T., "What Next for Human Gene Therapy?," BMJ 326:1410-11 (2003).
English Translation and Notice of Reasons for Rejection for Japanese Application No. 2014-517125 (May 9, 2016).
Office Action for U.S. Appl. No. 14/516,231 (Jun. 22, 2016).
Kappel et al., "Regulating Gene Expression in Transgenic Animals," Current Opinion in Biotechnology 3:548-53 (1992).
Kimmelman, J., "Recent Developments in Gene Transfer: Risk and Ethics," BMJ 350:79-82 (2005).
Mullins et al., "Transgenesis in Nonmurine Species," Hypertension 22(4):630-3 (1993).
Mullins et al., "Transgenesis in the Rat and Larger Mammals," J. Clin. Invest. 97(7):1557-60 (1996).
Raper, S.E., "Gene Therapy: the Good, the Bad, and the Ugly," Surgery 137(5):487-92 (2005).
Rosenberg et al., "Gene Therapist, Heal Thyself," Science 287:1751 (2000).
Touchette, N., "Gene Therapy: Not Ready for Prime Time," Nature Medicine 2(1):7-8 (1996).
Wigley et al., "Site-Specific Transgene Insertion: An Approach," Reprod. Fertil. Dev. 6:585-8 (1994).
Wolff, J.A., "The 'Grand' Problem of Synthetic Delivery," Nat. Biotechnol. 20:768-9 (2002).
Cameron, E.R., "Recent Advances in Transgenic Technology," Molecular Biotechnol. 7:253-265 (1997).
Couzin et al., "As Gelsinger Case Ends, Gene Therapy Suffers Another Blow," Science 307:1028 (2005).
Donsante et al., "AAV Vector Integration Sites in Mouse Hepatocellular Carcinoma," Science 317:477 (2007).

\* cited by examiner

CERAMIDE LEVELS IN THE TREATMENT AND PREVENTION OF INFECTIONS

This application is a national stage application under 35 U.S.C. 371 of PCT Application No. PCT/US2013/043608, filed May 31, 2013, which claims benefit of U.S. Provisional Patent Application Ser. No. 61/654,519, filed Jun. 1, 2012, which are hereby incorporated by reference in their entirety.

FIELD OF THE INVENTION

The present invention relates to normalizing ceramide levels to prevent and/or treat pathogenic infections in a subject with cystic fibrosis, Chronic Obstructive Lung Disease (COPD), and/or an open wound.

BACKGROUND OF THE INVENTION

Cystic Fibrosis ("CF") is the most common autosomal recessive disorder in Europe and the USA, impacting one in every 2500 children born in Western Countries. It is a disease caused by mutations of the CF transmembrane conductance regulator protein ("CFTR"). While this genetic mutation leads to several respiratory, reproductive and gastrointestinal complications, the primary cause of morbidity and mortality in these subjects results from the destructive effects of chronic pulmonary colonization with *Pseudomonas aeruginosa* ("*P. aeruginosa*"). Medical records indicate approximately 80% of subjects with CF will host *P. aeruginosa* by the age of 25. See Cystic Fibrosis Foundation Subject Registry: Annual Data Report (2010). In addition to the increased susceptibility to *P. aeruginosa*, CF lungs are characterized by chronic inflammation and progressive fibrosis. At present, the molecular mechanisms that mediate the hallmarks of CF disease, i.e., infection susceptibility, inflammation, and fibrosis, require definition.

*P. aeruginosa* infection of epithelial cells is initiated by contact of the pathogen with the cell surface. Several binding molecules for *P. aeruginosa* have been identified, including CFTR, Fibronectin, α5β1-integrin and glycolipids including asialo-GM1. See Pier et. al., "Role Of Mutant CFTR In Hypersusceptibility Of Cystic Fibrosis Subjects To Lung Infections," *Science.* 271, 64-67 (1996); Schroeder et. al., "CFTR Is A Pattern Recognition Molecule That Extracts *Pseudomonas aeruginosa* LPS From The Outer Membrane Into Epithelial Cells And Activates NF-kappa B Translocation," *Proc. Natl. Acad. Sci. U.S.A.* 99, pp. 6907-6912 (2002); deBentzmann et. al., "Asialo GM1 Is A Receptor For *Pseudomonas aeruginosa* Adherence To Regenerating Respiratory Epithelial Cells," *Infect. Immun.* 64(5) pp. 1582-1588 (1996); deBentzmann et. al., "*Pseudomonas aeruginosa* Adherence To Remodeling Respiratory Epithelium," *Eur. Respir. J.* 9 pp. 2145-2150 (1996); Roger et. al., "Fibronectin And α5β1-integrin Mediate Binding Of *Pseudomonas aeruginosa* To Repairing Airway Epithelium," *Eur. Respir. J.* 13 pp. 1301-1309 (1999); Saiman et. al., "*Pseudomonas aeruginosa* Pili Bind To AsialoGM1 Which Is Increased On The Surface Of Cystic Fibrosis Epithelial Cells," *J. Clin. Invest.* 92 pp. 1875-1880 (1993); and Davies et. al., "Reduction In The Adherence Of *Pseudomonas aeruginosa* To Native Cystic Fibrosis Epithelium With Anti-AsialoGM1 Antibody And Neuraminidase Inhibition," *Eur. Respir. J;* 13 pp. 565-570 (1999).

Therefore, identification of epithelial receptors for *P. aeruginosa* that are specifically altered in CF and involved in the high infection susceptibility of these subjects to *P. aeruginosa*, is an important consideration in the development of new strategies for CF—and concomitant pathogenic infection—prophylaxis and treatment. Such molecules would be ideal targets to prevent the initial contact of the pathogen with bronchial epithelial cells in CF subjects and, thus, to prevent the infection very early.

Current methods of treating and preventing disease pathogenesis in subjects afflicted with a disease or condition raise toxicity and efficacy concerns.

The present invention is directed to overcoming these deficiencies in the art by, for example, by correcting the abnormal expression of primary binding molecules of bacterial pathogens to bronchial epithelial cells in vivo through a unique membrane lipid mediated mechanism.

SUMMARY OF THE INVENTION

One aspect of the present invention is directed to a method for treating or preventing pathogenic infections in a subject having Cystic Fibrosis, Chronic Obstructive Lung Disease (COPD), and/or an open wound. This method involves selecting a subject having Cystic Fibrosis, COPD, and/or an open wound and administering to the selected subject a ceramidase under conditions effective to reduce ceramide and to treat or prevent the pathogenic infection in the selected subject.

Another aspect of the present invention relates to administering to the subject a ceramidase in combination with other agents to reduce ceramide or reduce infections. Such agents may include but not be limited to antibiotics, reagents to reduce mucus viscosity, chaperone agents to enhance the function of the Cystic Fibrosis transmembrane protein (CFTR), or acid sphingomyelinase inhibitors.

Another aspect of the present invention relates to selecting said subject based on the level of ceramide in their cells, tissues or fluids, and/or the level of an endogenous ceramidase enzyme.

BRIEF DESCRIPTION OF THE DRAWINGS

FIG. 1A is a representative section of wild type mice, CerS2-deficient mice, and Cystic Fibrosis mice lung stained with Cy3-anti-ceramide antibodies and then analyzed by confocal microscopy. FIG. 1B is a representative section of wild type mice, CerS2-deficient mice, and Cystic Fibrosis mice lung stained with the same antibody 2 hours after the mouse received a single inhalation of acid ceramidase ("AC"). Results are representative of at least 6 mice per group.

DETAILED DESCRIPTION OF THE INVENTION

Figures 1A, 1B:
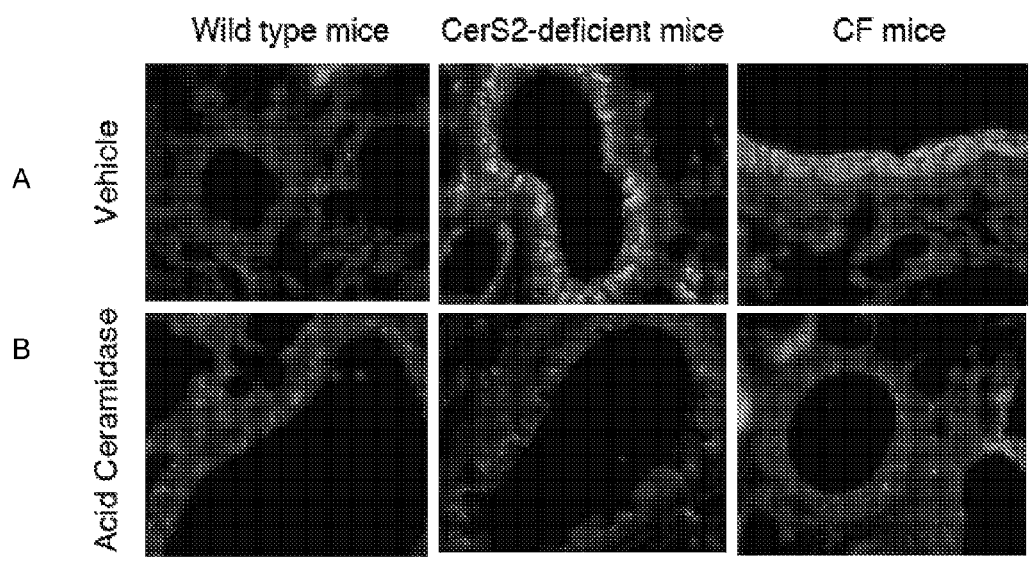
FIGS. 1A and 1B show paraffin embedded sections of mouse lungs.

In practicing the present invention, many conventional techniques in molecular biology, protein biochemistry, cell biology, immunology, microbiology and recombinant DNA are used. These techniques are well-known and are explained in, e.g., *Current Protocols in Molecular Biology*, Vols. I-III, Ausubel, Ed. (1997); Sambrook et al., *Molecular Cloning: A Laboratory Manual*, Second Ed. (Cold Spring Harbor Laboratory Press, Cold Spring Harbor, N.Y. (1989)); *DNA Cloning: A Practical Approach*, Vols. I and II, Glover, Ed. (1985); *Oligonucleotide Synthesis*, Gait, Ed. (1984); *Nucleic Acid Hybridization*, Hames & Higgins, Eds. (1985); *Transcription and Translation*, Hames & Higgins, Eds. (1984); *Animal Cell Culture*, Freshney, Ed. (1986); *Immobilized Cells and Enzymes* (IRL Press, 1986); Perbal, *A Practical Guide to Molecular Cloning*; the series, *Meth. Enzymol.*, (Academic Press, Inc., 1984); *Gene Transfer Vectors for Mammalian Cells*, Miller & Calos, Eds. (Cold Spring Harbor Laboratory, New York (1987)); and *Meth. Enzymol.*, Vols. 154 and 155, Wu & Grossman, and Wu, Eds., respectively, all of which are hereby incorporated by reference in their entirety. Methods to detect and measure levels of polypeptide gene expression products, i.e., gene translation level, are well-known in the art and include the use of polypeptide detection methods such as antibody detection and quantification techniques. See also, Strachan & Read, *Human Molecular Genetics*, Second Edition. (John Wiley and Sons, Inc., New York (1999), which is hereby incorporated by reference in its entirety.

It is to be appreciated that certain aspects, modes, embodiments, variations and features of the present invention are described below in various levels of detail in order to provide a substantial understanding of the present technology. The definitions of certain terms as used in this specification are provided below. Unless defined otherwise, all technical and scientific terms used herein generally have the same meaning as commonly understood by one of ordinary skill in the art to which this invention belongs.

Underlying disease conditions can predispose a subject to acute and/or chronic pathogenic infections. As used herein a "disease condition" refers to a pathological disease or condition of any kind or origin, which a subject harbors. Accordingly, disease conditions include the subject matter identified by the following diseases and/or terms including, but not limited to, e.g., a respiratory disease, lung disease, Cystic Fibrosis ("CF"), chronic obstructive pulmonary disease ("COPD"), emphysema, asthma, pulmonary fibrosis, chronic bronchitis, pneumonia, pulmonary hypertension, lung cancer, sarcoidosis, necrotizing pneumonia, asbestosis, aspergilloma, aspergillosis, acute invasive atelectasis, eosinophilic pneumonia, pleural effusion, pneumoconiosis, pneumocystosis, pneumothorax, pulmonary actinomycosis, pulmonary alveolar proteinosis, pulmonary anthracis, pulmonary arteriovenous malformation, pulmonary edema, pulmonary embolus, pulmonary histiocytosis X (eosinophilic granuloma), pulmonary nocardiosis, pulmonary tuberculosis, pulmonary veno-occlusive disease, rheumatoid lung disease, and/or an open wound. Such diseases typically manifest an increased susceptibility of a subject for pathogenic infection, i.e., compared to subjects not afflicted with a disease condition.

For example, subjects suffering from CF, COPD, and/or an open wound, may possess a high susceptibility for acquiring acute and/or chronic pathogenic infections, such as, e.g., bacterial, viral, fungal, protozoan, and/or prionic pathogenic infections. Bacterial pathogens include, without limitation, *Bacillus anthracis, Bordetella pertussis, Borrelia burgdorferi, Campylobacter jejuni, Chlamydia trachomatis, Clostridium botulinum, Clostridium tetani, Corynebacterium dipththeriae, Escherichia coli*, enterohemorrhagic *E. coli*, enterotoxigenic *E. coli, Haemophilus influenzae* type B and non-typable, *Helicobacter pylori, Legionella pneumophila, Listeria monocytogenes, Mycobacterium* spp., *Mycobacterium leprae, Mycobacterium tuberculosis, Neisseria gonorrhoeae, Neisseria meningitidis, Pneumococcus* spp., *Pseudomonas aeruginosa, Rickettsia, Salmonella* spp., *Shigella* spp., *Staphylococcus* spp., *Staphylococcus aureus, Streptococcus* spp., *Streptococcus pneumoniae, Streptococcus pyogenes, Streptococcus* B, Group A beta hemolytic *Streptococcus, Streptococcus mutans, Treponema pallidum, Vibrio cholerae*, and *Yersinia pestis*. In some embodiments, the pathogenic infection is a *Pseudomonas* infection. In some embodiments, the *Pseudomonas* infection is a *Pseudomonas aeruginosa* infection.

Viral pathogens include, without limitation, RNA viruses, DNA viruses, adenovirdiae (e.g., mastadenovirus and aviadeno virus), herpesviridae (e.g., herpes simplex virus 1, herpes simplex virus 2, herpes simplex virus 5, and herpes simplex virus 6), leviviridae (e.g., levivirus, enterobacteria phage MS2, allolevirus), poxyiridae (e.g., chordopoxyirinae, parapoxvirus, avipoxvirus, capripoxvirus, leporipoxvirus, suipoxvirus, molluscipox virus, and entomopoxyirinae), papovaviridae (e.g., polyomavirus and papillomavirus), paramyxoviridae (e.g., paramyxovirus, parainfluenza virus 1, mobillivirus such as measles virus, rubulavirus (such as mumps virus), pneumonoviridae (e.g., pneumovirus, human respiratory syncytial virus), metapneumovirus (e.g., avian pneumovirus and human metapneumo virus), picornaviridae (e.g., enterovirus, rhinovirus, hepatovirus such as human hepatitis A virus, cardiovirus, and apthovirus), reoviridae (e.g., orthoreo virus, orbivirus, rotavirus, cypo virus, fijivirus, phytoreo virus, and oryzavirus), retroviridae (e.g., mammalian type B retroviruses, mammalian type C retroviruses, avian type C retroviruses, type D retrovirus group, BLV-HTLV retroviruses, lentivirus (such as human immunodeficiency virus 1 and human immunodeficiency virus 2; and spuma virus), flaviviridae (e.g., hepatitis C virus), hepadnaviridae (e.g., hepatitis B virus), togaviridae (e.g., alphavirus—such as sindbis virus and rubivirus, such as rubella virus), rhabdoviridae (e.g., vesiculovirus, lyssavirus, ephemera virus, cytorhabdovirus, and necleorhabdovirus), arenaviridae (e.g., arenavirus, lymphocytic choriomeningitis virus, Ippy virus, and lassa virus), and coronaviridae (e.g., coronavirus and torovirus), Cytomegalovirus (mononucleosis), Dengue virus (dengue fever, shock syndrome), Epstein-Barr virus (mononucleosis, Burkitt's lymphoma), Human T-cell lymphotropic virus type 1 (T-cell leukemia), Influenza A, B, and C (respiratory disease), Japanese encephalitis virus (pneumonia, encephalopathy), Poliovirus (paralysis), Rhinovirus (common cold), Rubella virus (fetal malformations), Vaccinia virus (generalized infection), Yellow fever virus (jaundice, renal and hepatic failure), and Varicella zoster virus (chickenpox).

Pathogenic fungi include, without limitation, the genera *Aspergillus* (e.g., *Aspergillus fumigates*), *Blastomyces, Can-* dida (e.g., *Candida albicans*), *Coccidiodes*, *Cryptococcus*, *Histoplasma*, *Phycomyces*, *Tinea corporis*, *Tinea unguis*, *Sporothrix schenckii*, and *Pneumocystis carinii*. Pathogenic protozoan include, without limitation, *Trypanosome* spp., *Leishmania* spp., *Plasmodium* spp., *Entamoeba* spp., and *Giardia* spp. such as *Giardia lamblia*

Because the molecular mechanisms which precipitate increased susceptibility to a pathogenic infection in subjects afflicted with a disease condition are not well understood, elucidating the pathology of, for example, *P. aeruginosa*, with respect to cellular attachment and internalization, are important considerations for preventing and treating subjects prone to acquiring such infections.

Integrins are receptor molecules which function to coordinate cellular processes relating to, e.g., attachment and adhesion. Integrins, however, are not characteristically expressed at the luminal surface of normal, healthy bronchial epithelial cells, and epithelial cell-layer tight junctions prevent the contact of bronchial pathogens with the basolateral pole of epithelial cells—where integrins typically reside.

The term "elevated levels" or "higher levels" as used herein refers to levels of a measurable marker, molecule, or protein, such as, for example, ceramide, that are higher than what would normally be observed in a comparable sample from control or normal subjects, i.e., a reference value or control levels or normalized levels. In some embodiments, "control levels", i.e., normal levels, refer to a range of that would normally be expected to be observed in a sample from a subject that does not have a disease condition. A control level may be used as a "reference level" for comparative purposes, as further detailed, infra. "Elevated levels" therefore refer to levels that are above the range of control levels. The ranges accepted as "elevated levels" or "control levels" are dependent on a number of factors. The skilled artisan is capable of considering the relevant factors and establishing appropriate reference ranges for "control values" and "elevated values" of the present invention. For example, a series of samples from control subjects and subjects diagnosed with CF can be used to establish ranges that are "normal" or "control" levels and ranges that are "elevated" or "higher" compared to the control range or level.

Ceramidases are enzymes capable of hydrolyzing ceramide into fatty acids and a sphingoid base (sphingosine), which is involved in cellular proliferation and intracellular signal transduction. The ceramidase, after enzymatic activation, facilitates ceramide hydrolysis into individual fatty acid and sphingosine components. See Gatt, "Enzymic Hydrolysis and Synthesis of Ceramide," *J. Biol. Chem.* 238:3131-3 (1963); Gatt, "Enzymatic Hydrolysis of Sphingolipids. 1. Hydrolysis and Synthesis of Ceramides by an Enzyme from Rat Brain," *J. Biol. Chem.* 241:3724-31 (1966); Hassler & Bell, "Ceramidase: Enzymology and Metabolic Roles," *Adv. Lip. Res.* 26:49-57 (1993), all of which are hereby incorporated by reference in their entirety. There is no de novo pathway for cells to generate sphingosine, and it is therefore only generated by ceramide hydrolysis pursuant to the enzymatic action of a ceramidase.

One aspect of the present invention is directed to a method for treating or preventing pathogenic infections in a subject having Cystic Fibrosis, COPD, and/or an open wound. This method of the present invention involves selecting a subject having Cystic Fibrosis, COPD, and/or an open wound and administering to the selected subject a ceramidase under conditions effective to reduce ceramide and to treat or prevent the pathogenic infection in the selected subject.

As described herein, an "open wound" refers to a type of injury in which an epithelial layer, i.e., skin, is torn, cut, and/or punctured. In some embodiments, an open wound refers to a sharp injury which damages the dermis of the skin and concomitantly increases the chance of acquiring an infection. The term "open wound" also encompasses burns.

The methods of the present invention further involve selecting the subject based on elevated ceramide levels compared to a reference level for a subject not having Cystic Fibrosis, COPD, and/or an open wound. As used herein, the term "reference level" refers to a level of a substance, e.g., ceramide, which may be of interest for comparative purposes. In some embodiments, a reference level may be the level or concentration of a protein expressed as an average of the level or concentration from samples of a control population of healthy (disease-free and/or pathogen-free) subjects. In other embodiments, the reference level may be the level in the same subject at a different time, e.g., before the present invention is employed, such as the level determined prior to the subject developing a disease, disease condition, and/or pathogenic infection, prior to initiating therapy, such as, for example, ceramidase therapy, or earlier in the therapy.

Exemplary methods of comparing ceramide levels between a subject and a reference level include, but are not limited to, comparing differences in detected ceramide levels, based on results of one or more protein assays as further described, infra. In some embodiments, ceramide levels are higher in the presence of a disease condition as described herein. A subject with, or a sample possessing, a lower detected ceramide level compared to a reference level would indicate that the subject may not require ceramidase therapy and/or the subject may not have a disease condition as described herein.

The method of the present invention further relates to selecting a subject based on ceramide level in lung epithelium, nasal epithelium, mucus, and/or cells isolated from an open wound site. In some embodiments, administering is carried out under conditions effective to normalize ceramide levels in the subjects' respiratory epithelia, mucus, or cells at an open wound site. In some embodiments, the ceramidase is an acid ceramidase ("AC"), such as, but not limited to, the AC's listed in Table 1 below.

Acid ceramidase (N-acylsphingosine deacylase, I.U.B.M.B. Enzyme No. EC 3.5.1.23) is one particular ceramidase responsible for the catabolism of ceramide. Due to its involvement in the human genetic disorder Farber Lipogranulomatosis, AC is one of the most extensively studied members of the ceramidase enzyme family. The protein has been purified from several sources, and the human and mouse cDNAs and genes have been obtained. See Bernardo et al., "Purification, Characterization, and Biosynthesis of Human Acid Ceramidase," *J. Biol. Chem.* 270:11098-102 (1995); Koch et al., "Molecular Cloning and Characterization of a Full-length Complementary DNA Encoding Human Acid Ceramidase. Identification of the First Molecular Lesion Causing Farber Disease," *J. Biol. Chem.* 2711:33110-5 (1996); Li et al., "Cloning and Characterization of the Full-length cDNA and Genomic Sequences Encoding Murine Acid Ceramidase," *Genomics* 50:267-74 (1998); Li et al., "The Human Acid Ceramidase Gene (ASAH): Chromosomal Location, Mutation Analysis, and Expression," *Genomics* 62:223-31 (1999), all of which are hereby incorporated by reference in their entirety.

As described above, AC is a ceramidase which catalyzes the hydrolysis of ceramide to sphingosine and free fatty acid. See Bernardo et al., "Purification, Characterization, and Biosynthesis of Human Acid Ceramidase," *J. Biol. Chem.* 270(19):11098-102 (1995), which is hereby incorporated by reference in its entirety. Mature AC is a ~50 kDa protein composed of an α-subunit (~13 kDa) and a β-subunit (~40 kDa). See Bernardo et al., "Purification, Characterization, and Biosynthesis of Human Acid Ceramidase," *J. Biol. Chem.* 270(19):11098-102 (1995), which is hereby incorporated by reference in its entirety. It is produced through cleavage of the AC precursor protein (see Ferlinz et al., "Human Acid Ceramidase: Processing, Glycosylation, and Lysosomal Targeting," *J. Biol. Chem.* 276(38):35352-60 (2001), which is hereby incorporated by reference in its entirety), which is the product of the AsahI gene (NCBI UniGene GeneID No. 427, which is hereby incorporated by reference in its entirety).

AC function and/or activity, moreover, is directly related to surrounding pH. In fact, it is normally found within lysosomes with an acidic pH of ~4.5, and in the absence of AC activity in patients with Farber Lipogranulomatosis ceramides accumulate in lysosomes.

In addition, recent studies have shown that an increase in intracellular compartment pH reduces AC activity/function by up to 90%. See Teichgräber et al., "Ceramide Accumulation Mediate Inflammation, Cell Death And Infection Susceptibility In Cystic Fibrosis," *Nat Med.* 14(4), pp. 382-391 (2008), which is hereby incorporated by reference in its entirety. In some respects, these results mimic Farber's disease, which is caused by a deficiency of AC and results in an accumulation of ceramide. See He et al., "Purification And Characterization Of Recombinant, Human Acid Ceramidase," *J. Biol. Chem.* 278, 32978-32986 (2003), which is hereby incorporated by reference in its entirety. Furthermore, at a pH of 5.9, AC has been shown to possess a reverse activity-producing ceramide instead of consuming it. See id. This activity in concert with impaired Asm function—at increasing vesicular pH levels—can result in a net accumulation of ceramide. See Teichgräber et al., "Ceramide Accumulation Mediate Inflammation, Cell Death And Infection Susceptibility In Cystic Fibrosis," *Nat Med.* 14(4), pp. 382-391 (2008), which is hereby incorporated by reference in its entirety.

Other studies have shown that CFTR deficiency in alveolar macrophages result in a lysosomal pH shift from pH 4.5 to at least pH 5.9. See Di et al. "CFTR Regulates Phagosome Acidification In Macrophages And Alters Bactericidal Activity," *Nat. Cell Biol.* 8, 933-944 (2006), which is hereby incorporated by reference in its entirety. As such, the present invention surprisingly functions to prevent and/or treat pathogenic infections in CF subjects at least because AC would not be expected to decrease elevated ceramide levels in CF subjects possessing increased lysosomal pH. Moreover, AC would not be expected to function on the accumulating ceramide in the lung epithelial cell membrane.

The AC's that can be used in the context of the present invention include, without limitation, those set forth in Table 1 below. In all aspects of the present invention, the AC can be homologous (i.e., derived from the same species) or heterologous (i.e., derived from a different species) to the tissue, cells, and/or subject being treated.

TABLE 1

Exemplary Acid Ceramidase Family Members

| | |
|---|---|
| *Homo sapiens* | |
| UniProt | Q13510, Q9H715, Q96AS2 |
| OMIM | 228000 |
| NCBI Gene | 427 |
| NCBI RefSeq | NP_808592, NP_004306 |

TABLE 1-continued

Exemplary Acid Ceramidase Family Members

| | |
|---|---|
| NCBI RefSeq | NM_177924, NM_004315 |
| NCBI UniGene | 427 |
| NCBI Accession | Q13510, AAC73009 |
| *Mus musculus* | |
| UniProt | Q9WV54, Q3U8A7, Q78P93 |
| NCBI Gene | 11886 |
| NCBI RefSeq | NP_062708 |
| NCBI RefSeq | NM_019734 |
| NCBI UniGene | 11886 |
| NCBI Accession | AK151208, AK034204 |
| *Gallus gallus* | |
| UniProt | Q5ZK58 |
| NCBI Gene | 422727 |
| NCBI RefSeq | NP_001006453 |
| NCBI RefSeq | NM_001006453 |
| NCBI UniGene | 422727 |
| NCBI Accession | CAG31885, AJ720226 |
| *Pan troglodytes* | |
| NCBI Gene | 464022 |
| NCBI RefSeq | XP_519629 |
| NCBI RefSeq | XM_519629 |
| NCBI UniGene | 464022 |
| *Caenorhabditis elegans* | |
| UniProt | O45686 |
| IntAct | O45686 |
| NCBI Gene | 173120 |
| NCBI RefSeq | NP_493173 |
| NCBI RefSeq | NM_060772 |
| NCBI UniGene | 173120 |
| NCBI Accession | O45686, CAB05556 |
| *Danio rerio* | |
| UniProt | Q5XJR7 |
| NCBI Gene | 450068 |
| NCBI RefSeq | NP_001006088 |
| NCBI RefSeq | NM_001006088 |
| NCBI UniGene | 450068 |
| NCBI Accession | AAH83231, CB360968 |
| *Rattus norvegicus* | |
| UniProt | Q6P7S1, Q9EQJ6 |
| NCBI Gene | 84431 |
| NCBI RefSeq | NP_445859 |
| NCBI RefSeq | NM_053407 |
| NCBI UniGene | 84431 |
| NCBI Accession | AAH61540, AF214647 |

In some embodiments, determining the level of ceramide and/or AC concentration and/or activity is carried out prior to treatment. Assays suitable for determining ceramide concentrations and/or ceramidase levels or activity are readily apparent to the skilled artisan. Suitable methods include, for example, activity assays (see Eliyahu et al., "Acid Ceramidase is a Novel Factor Required for Early Embryo Survival," *FASEB J.* 21(7):1403-9 (2007), which is hereby incorporated by reference in its entirety, and well known techniques, such as, western blotting to determine the relative amount of ceramidase protein and/or activity present in the sample (where a higher amount of ceramidase protein correlates to a higher ceramidase activity level). See Eliyahu et al., "Acid Ceramidase is a Novel Factor Required for Early Embryo Survival," *FASEB J.* 21(7):1403-9 (2007), which is hereby incorporated by reference in its entirety.

As used herein, the term "assay" refers to an assay for detecting the presence or absence of ceramide and/or ceramidase, in a given sample of a bodily fluid. Also included are quantitative assays, which measure the amount of a substance in a sample. As used herein, the term "sample" is used in its broadest sense. In one sense, it is meant to include a specimen or culture obtained from biological samples. The bodily fluid sample is selected from the group consisting of serum, synovial fluid, cerebrospinal fluid, and peritoneal fluid. Of particular interest are samples that are serum. Those skilled in the art will recognize that plasma or whole blood or a sub-fraction of whole blood may also be used. Biological fluid samples may be obtained from animals (including humans) and include blood products, such as plasma, serum and the like. In some embodiments, the sample contains a level of ceramide or ceramidase, which can be readily ascertained by the methods described herein and those well known in the art.

Immunoassays, in their most simple and direct sense, are binding assays involving binding between antibodies and antigen. Many types and formats of immunoassays are known and all are suitable for detecting, e.g., ceramide levels. Examples of immunoassays are enzyme linked immunosorbent assays ("ELISAs"), enzyme linked immunospot assay ("ELISPOT"), radioimmunoassays ("RIA") (see Ferlinz et al., "Human Acid Ceramidase: Processing, Glycosylation, and Lysosomal Targeting," *J. Biol. Chem.* 276(38):35352-60 (2001), which is hereby incorporated by reference in its their entirety, radioimmune precipitation assays ("RIPA"), immunobead capture assays, dot blotting, gel-shift assays, flow cytometry, immunohistochemistry, fluorescence microscopy, protein arrays, multiplexed bead arrays, magnetic capture, in vivo imaging, fluorescence resonance energy transfer ("FRET"), and fluorescence recovery/localization after photobleaching ("FRAP/FLAP"). The steps of various useful immunodetection methods have been described in the scientific literature, such as, e.g., Maggio et al., *Enzyme-Immunoassay* (1987) and Nakamura, et al., "Enzyme Immunoassays: Heterogeneous and Homogeneous Systems, Handbook of Experimental Immunology," Vol. 1: *Immunochemistry*, 27.1-27.20 (1986), each of which is incorporated herein by reference in its entirety.

In general, immunoassays involve contacting a sample suspected of containing a molecule or protein of interest (such as, ceramide and/or ceramidase) with an antibody to the molecule or protein of interest, under conditions effective to allow the formation of immunocomplexes. In this regard, the skilled artisan will be able to assess the presence and or level of specific molecules or proteins of interest in a given sample.

Immunoassays can include methods for detecting or quantifying the amount of a molecule or protein of interest in a sample, which methods generally involve the detection or quantitation of any immune complexes formed during the binding process. In general, the detection of immunocomplex formation is well known in the art and can be achieved through the application of numerous approaches. These methods are generally based upon the detection of a label or marker, such as any radioactive, fluorescent, biological or enzymatic tags or any other known label. See, for example, U.S. Pat. Nos. 3,817,837; 3,850,752; 3,939,350; 3,996,345; 4,277,437; 4,275,149 and 4,366,241, each of which is incorporated herein by reference in its entirety.

One particularly effective non-specific assay used to detect total proteins is the Bradford protein assay. See Bradford, M. M., "A Rapid and Sensitive Method for the Quantitation of Microgram Quantities of Proteins Utilizing the Principle of Protein-Dye Binding," *Anal. Biochem.* 72:248-254 (1976), which is hereby incorporated by reference in its entirety.

The Bradford protein assay uses a dye stock of Coomassie Blue G (C.I. #42655) (100 mg), which is dissolved in 50 mL of methanol. The solution is added to 100 mL of 85% $H_3PO_4$, and diluted to 200 mL with water, resulting in a dark red. The final reagent concentrations of the assay are 0.5 mg/mL Coomassie Blue G, 25% methanol, and 42.5% $H_3PO_4$. The assay reagent of the Bradford assay is prepared by diluting 1 part dye stock with 4 parts distilled $H_2O$. The resulting color should be brown with a pH of 1.1. A series of protein standards are prepared in the same buffer as the samples to be assayed, using bovine serum albumin ("BSA") with concentrations of 0, 250, 500, 750, and 1500 µg/mL for a standard assay. The absorbance is read at 595 nm for standard assay procedure and 450 nm for a micro assay (Dynex Technologies, Chantilly, Va.), and the ratio of the absorbances, 595 nm over 450 nm, was used for standard curve calculations. See Zor, et al., "Linearization of the Bradford Protein Assay Increases Its Sensitivity: Theoretical and Experimental Studies," *Anal. Biochem.* 236:302-308 (1996), which is hereby incorporated by reference in its entirety.

In some embodiments, the methods of the present invention are carried out by administering an AC precursor protein, which is then converted into an active acid ceramidase protein by the cell. In particular, the AC precursor protein undergoes autoproteolytic cleavage into the active form (composed of α- and β-subunits). This is promoted by the intracellular environment, and based on highly conserved sequences at the cleavage site of AC precursor proteins across species, is expected to occur in most, if not all, cell types. Suitable acid ceramidase precursor proteins include those set forth in Table 1, supra. As will be apparent to the skilled artisan, the precursor protein could optionally be contained in a culture medium to which the cell is exposed. Embodiments in which the precursor protein is taken up by the host subject or cell of interest and converted into active acid ceramidase is thus contemplated.

Yet another approach for administering proteins or polypeptide agents of the present invention, e.g., AC, involves preparation of chimeric proteins according to U.S. Pat. No. 5,817,789 to Heartlein et al., which is hereby incorporated by reference in its entirety. The chimeric protein can include a ligand domain and the polypeptide agent (e.g., AC, AC precursor protein). The ligand domain is specific for receptors located on a target cell. Thus, when the chimeric protein is delivered to the subject, cell, and/or culture medium, the chimeric protein will be internalized.

Depending on the level or activity of a substance, e.g., ceramide and/or ceramidase, one or more additional agents may be administered in combination with the ceramidase, e.g., AC, in accordance with the methods of the present invention. In some embodiments, the one or more additional agents are selected from the group consisting of one or more additional ceramide reducing agents, one or more acid sphingomyelinase inhibitors, one or more agents to reduce infection, and combinations thereof. Suitable agents to reduce infection include antibiotics (e.g., inhaled Tobramycin, TOBI), reagents that block binding of pathogens to lung epithelium, reagents to reduce mucus viscosity (e.g., Dornase alfa, Pulmozyme), chaperone reagents to enhance missing protein function (e.g., Ivacaftor, Kalydeco), and combinations thereof. In some embodiments, the ceramidase, e.g., AC, is administered simultaneously, separately, or sequentially with the one or more additional agents.

As used herein, the term "simultaneous" therapeutic use refers to the administration of at least two active ingredients by the same route and at the same time or at substantially the same time. As used herein, the term "separate" therapeutic use refers to an administration of at least two active ingredients at the same time or at substantially the same time by different routes. As used herein, the term "sequential" therapeutic use refers to administration of at least two active ingredients at different times, the administration route being identical or different. More particularly, sequential use refers to the whole administration of one of the active ingredients before administration of the other or others commences. It is thus possible to administer one of the active ingredients over several minutes, hours, or days before administering the other active ingredient or ingredients. There is no simultaneous treatment in this case.

Administration can be accomplished either via systemic administration to the subject or via targeted administration to affected tissues, organs, and/or cells. The therapeutic agent (i.e., AC, AC precursor protein, nucleic acid encoding AC/AC precursor protein) may be administered to a non-targeted area along with one or more agents that facilitate migration of the therapeutic agent to (and/or uptake by) a targeted tissue, organ, or cell. Additionally and/or alternatively, the therapeutic agent itself can be modified to facilitate its transport to (and uptake by) the desired tissue, organ, or cell, as will be apparent to one of ordinary skill in the art.

Any suitable approach for delivery of the agents can be utilized to practice this aspect of the present invention. Typically, the therapeutic agent will be administered to a patient in a vehicle that delivers the therapeutic agent(s) to the target cell, tissue, or organ. Exemplary routes of administration include, without limitation, by intratracheal inoculation, aspiration, airway instillation, aerosolization, nebulization, intranasal instillation, oral or nasogastric instillation, intraperitoneal injection, intravascular injection, topically, transdermally, parenterally, subcutaneously, intravenous injection, intra-arterial injection (such as via the pulmonary artery), intramuscular injection, intrapleural instillation, intraventricularly, intralesionally, by application to mucous membranes (such as that of the nose, throat, bronchial tubes, genitals, and/or anus), or implantation of a sustained release vehicle.

In some embodiments, a ceramidase, e.g., AC, is administered orally, topically, intranasally, intraperitoneally, intravenously, subcutaneously, or by aerosol inhalation. In some embodiments, a ceramidase, e.g., AC, is administered via aerosol inhalation. In some embodiments, the ceramidase and/or additional agents can be incorporated into pharmaceutical compositions suitable for administration, as described herein.

The agents of the present invention, e.g., AC, may be orally administered, for example, with an inert diluent, or with an assimilable edible carrier, or they may be enclosed in hard or soft shell capsules, or they may be compressed into tablets, or they may be incorporated directly with the food of the diet. For oral therapeutic administration, these active compounds may be incorporated with excipients and used in the form of tablets, capsules, elixirs, suspensions, syrups, and the like. Such compositions and preparations should contain at least 0.1% of the agent. The percentage of the agent in these compositions may, of course, be varied and may conveniently be between about 2% to about 60% of the weight of the unit. The amount of the agent in such therapeutically useful compositions is such that a suitable dosage will be obtained.

The tablets, capsules, and the like may also contain a binder such as gum tragacanth, acacia, corn starch, or gelatin; excipients such as dicalcium phosphate; a disintegrating agent such as corn starch, potato starch, or alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

The agents, e.g., AC, may also be administered parenterally. Solutions or suspensions of the agent can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

The agents, e.g., AC, according the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form.

Exemplary delivery devices include, without limitation, nebulizers, atomizers, liposomes (including both active and passive drug delivery techniques) (Wang & Huang, "pH-Sensitive Immunoliposomes Mediate Target-cell-specific Delivery and Controlled Expression of a Foreign Gene in Mouse," *Proc. Nat'l Acad. Sci. USA* 84:7851-5 (1987); Bangham et al., "Diffusion of Univalent Ions Across the Lamellae of Swollen Phospholipids," *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; and U.S. Pat. No. 5,059,421 to Loughrey et al.; Wolff et al., "The Use of Monoclonal Anti-Thy1 IgG1 for the Targeting of Liposomes to AKR-A Cells in Vitro and in Vivo," *Biochim. Biophys. Acta* 802:259-73 (1984), each of which is hereby incorporated by reference in its entirety), transdermal patches, implants, implantable or injectable protein depot compositions, and syringes. Other delivery systems which are known to those of skill in the art can also be employed to achieve the desired delivery of the therapeutic agent to the desired organ, tissue, or cells.

Administration can be carried out as frequently as required and for a duration that is suitable to provide effective prophylaxis or efficacy against a pathogen. For example, administration can be carried out with a single sustained-release dosage formulation or with multiple daily doses.

The amount to be administered will, of course, vary depending upon the treatment regimen. Generally, an agent is administered to achieve an amount effective for improving pathogenic clearance. Thus, a therapeutically effective amount can be an amount which is capable of at least partially preventing and/or treating a pathogenic infection. This includes, without limitation, delaying the onset of infection. The dose required to obtain an effective amount may vary depending on the agent, formulation, and individual to whom the agent is administered.

Dosage, toxicity and therapeutic efficacy of the agents or compositions of the present invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit high therapeutic indices may be desirable. While compositions that exhibit toxic side effects may be used, care should be taken to design a delivery system that targets such compositions to the site of affected tissue in order to minimize potential damage to uninfected cells and, thereby, reduce side effects.

As such, the ceramidase is administered in a therapeutically effective amount, in some embodiments. As used herein, the terms "therapeutically effective amount", "effective amount", or "pharmaceutically effective amount" of an agent, protein, compound, and/or composition, is a quantity sufficient to achieve a desired therapeutic and/or prophylactic effect, e.g., an amount which results in the prevention of, or a decrease in, the symptoms associated with a disease that is being treated.

The effective amount of an agent or composition of the present invention administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with one or more additional therapeutic compounds.

Typically, the therapeutic agent will be administered as a pharmaceutical formulation that includes the therapeutic agent and any pharmaceutically acceptable adjuvants, carriers, excipients, and/or stabilizers, and can be in solid or liquid form, such as tablets, capsules, powders, solutions, suspensions, or emulsions. The compositions preferably contain from about 0.01 to about 99 weight percent, more preferably from about 2 to about 60 weight percent, of therapeutic agent together with the adjuvants, carriers and/or excipients. In some embodiments, an effective amount ranges from about 0.001 mg/kg to about 500 mg/kg body weight of the subject. In some embodiments, the effective amount of the agent ranges from about 0.05 mg/kg to about 30 mg/kg, from about 0.1 mg/kg to about 30 mg/kg, from about 1 mg/kg to about 25 mg/kg, from about 1 mg/kg to about 20 mg/kg, or from about 1 or 2 mg/kg to about 15 mg/kg.

The agents, e.g., AC, of the present invention can be administered at various times. Ceramidase, e.g., AC, is administered prior to the onset of infection in some embodiments. In other embodiments, the ceramidase, e.g., AC, is administered after the onset of infection. Further still, the ceramidase, e.g., AC, may be administered prior to and after the onset of infection according to some embodiments of the present invention.

Another aspect of the present invention relates to methods of monitoring the effectiveness of a therapy in a subject having a pathogenic infection and an underlying disease condition. The method includes selecting a subject, providing a baseline ceramide level in a bodily fluid sample from the selected subject before the therapy, and treating the pathogenic infection with the therapy, which, for example, can be the therapeutic administration of a ceramidase such as, e.g., AC. The method further includes detecting a post-therapy ceramide level in a bodily fluid sample from the selected subject following the therapy, comparing the baseline ceramide level with the post-therapy ceramidase level, and identifying whether the therapy has been effective based on the comparing and/or the pathology of the pathogenic infection.

In another aspect of the present invention, a kit or reagent system for using or administering the agents of the present invention. Such kits will contain a reagent combination including the particular elements required to conduct an assay according to the methods disclosed herein. The reagent system is presented in a commercially packaged form, as a composition or admixture where the compatibility of the reagents will allow, in a test device configuration, or more typically as a test kit, i.e., a packaged combination of one or more containers, devices, or the like holding the necessary reagents, and preferably including written instructions for the performance of assays. The kit may be adapted for any configuration of an assay and may include compositions for performing any of the various assay formats described herein.

Reagents useful for the disclosed methods can be stored in solution or can be lyophilized. When lyophilized, some or all of the reagents can be readily stored in microtiter plate wells for easy use after reconstitution. It is contemplated that any method for lyophilizing reagents known in the art would be suitable for preparing dried down reagents useful for the disclosed methods.

Having now generally described the invention, the same will be more readily understood through reference to the following examples which are provided by way of illustration, and are not intended to be limiting of the present invention, unless specified.

EXAMPLES

Example 1

Mice

B6.129P2(CF/3)-Cfr$^{TgH(neoim)Hgu}$ ("CF$^{MHH}$") congenic mice were produced through the inbreeding of the original Cftr$^{TgH(neoim)Hgu}$ mutant mouse, which was generated by insertional mutagenesis in exon 10 of the Cftr gene. See Charizopoulou et. al., "Instability Of The Insertional Mutation In Cftr$^{TgH(neoim)Hgu}$ Cystic Fibrosis Mouse Model," *BMC Genet.* 5 p. 6 (2004), which is hereby incorporated by reference in its entirety. This congenic Cftr$^{MHH}$ strain was then backcrossed into the B6 background. These mice still express low levels of CFTR, and can thus be fed a standard mouse diet. They exhibit normal development, but also display pulmonary pathology typical for CF. They are herein referred to as "CF" Mice. See Teichgräber et. al., "Ceramide Accumulation Mediate Inflammation, Cell Death And Infection Susceptibility In Cystic Fibrosis," *Nat Med.* 14(4), pp. 382-391 (2008); Wolbeling et. al., "Head-out Spirometery Accurately Monitors the Course of *Pseudomonas aeruginosa* Lung Infection in Mice," *Respiration* 80:340-6 (2010), which is hereby incorporated by reference in its entirety. Syngenic B6 mice were used as controls.

For some experiments, Cftr$^{tm1Unc}$-Tg$^{(FABPCFTR)}$ mice ("Cftr$^{-/-}$", purchased from The Jackson Laboratory, Bar Harbor, Me.) were backcrossed for more than 10 generations with C57BL/6 mice. The mice are completely deficient in Cftr in all organs except the intestine, where they express human CFTR which is under the control of a fatty acid binding protein ("FABP") promoter. The transgene prevents intestinal obstruction and enables feeding with a normal diet. Again, B6 mice were used as controls. No major differences were observed in experiments which employed both the Cftr$^{-/-}$ and Cftr$^{MHH}$ strains.

For other experiments, mice deficient in the enzyme ceramide synthase 2 were used. These mice (CerS2-/-) were generated by disruption of the first intron of the CerS2 mouse gene. They do not live beyond ~16 months and accumulate C16 ceramide in most tissues (Pewzner-Jung et al., "A Critical Role of Ceramide Synthase 2 in Liver Homeostasis I. Alterations in The Lipid Metabolic Pathway," *J Biol. Chem.* 285:10902 (2010), which is hereby incorporated by reference in its entirety).

The mice were housed and bred within isolated cages in the vivarium of the University Hospital, University of Duisburg-Essen, Germany. They were repeatedly evaluated for a panel of common murine pathogens according to the 2002 recommendations of the Federation of European Laboratory Animal Science Associations. The mice were free of all pathogens. Procedures performed on the animals were approved by the Bezirksregierung Duesseldorf, Duesseldorf, Germany.

Example 2

Antibodies and Reagents

All ceramide stainings were performed using the monoclonal mouse anti-ceramide antibody clone S58-9 (Glycobiotech) that was visualized with Cy3-donkey-anti-mouse IgM F(ab)$_2$ fragments (Jackson #715-166-020) or Cy5-coupled donkey-anti-mouse-IgM antibody (Jackson #715-176-020). Recombinant human acid ceramidase was produced in Chinese Hamster Ovary ("CHO") cells and purified from the media as previously described. He et al., *J Biol. Chem.* 278:32978-86 (2003), which is hereby incorporated by reference in its entirety.

Example 3

Bacteria

The laboratory strain American Type Culture Collection 27853 *P. aeruginosa* and the previously described clinical *P. aeruginosa* isolate ("762") were used. Bacteria were plated from frozen stocks on fresh Tryptic Soy Agar plates (TSA; Becton Dickinson), grown at 37° C. for 14-16 hours and resuspended in 40 mL of 37° C. warmed Tryptic Soy Broth (Becton Dickinson) to an optic density of 0.225 at 550 nm. The bacterial suspension was then incubated at 37° C. for 1 hr with 125 rpm shaking to attain bacteria in the early logarithmic growth phase. See Grassmé et. al., "Host Defense Against *Pseudomonas aeruginosa* Requires Ceramide-Rich Membrane Rafts," *Nat Med.* 9(3):322-330 (2003), which is hereby incorporated by reference in its entirety. Bacteria were then washed twice and resuspended in warmed RPMI-1640 medium (Invitrogen) supplemented with 10 mM HEPES (RPMI+HEPES). The final concentration of bacteria was quantified by photospectrometry.

Example 4

In Vivo Immunohistochemistry

For immunohistochemical evaluation of murine bronchial epithelial cells, mice were sacrificed by cervical dislocation and immediately perfused via the right heart with ice cold normal saline for two minutes at low pressure. This was followed by cardiac perfusion with 4% PBS-buffered PFA for 10-15 minutes. After this initial clearance of blood and fixation, the lungs were removed and further fixed in 4% PFA for 24-36 hrs. The tissue was serially dehydrated using an ethanol to xylol gradient and then embedded in paraffin.

The samples were then sectioned at 7 μm, dewaxed, re-hydrated, and treated with Pepsin (Invitrogen) for 15 min at 37° C. They were then washed with water and PBS and blocked for 10 min at room temperature with PBS and 0.05% Tween 20 (Sigma) and 1% FCS. The samples were then consecutively stained with primary antibodies in H/S+ 1% FCS at room temperature for 45 min. Samples were washed between the stainings twice with PBS+0.05% Tween 20 and once with PBS. The tissue was secondarily labeled with fluorescent-coupled secondary antibodies in H/S+1% FCS in the dark for 30 minutes. Tissue was again washed twice with PBS+0.05% Tween 20, once with PBS and finally embedded in Mowiol. Samples were evaluated using a confocal microscope as described below.

Example 5

Inhalation and In Vivo Infection

*P. aeruginosa* was prepared as described above and resuspended in RPMI-1640 plus 10 mM HEPES to a final concentration of 1×10$^8$ CFU in 20 μL medium. They were then inoculated using a plastic-coated 30-gauge needle, which was inserted 2 mm into the nose. Bacterial numbers were quantified in mouse lungs 2 hrs after infection. Mice were sacrificed and the lungs were removed, homogenized, and lysed in 5 mg/mL Saponin to release intracellular bacteria. The samples were then washed in sterile PBS, diluted, and plated in duplicate on TSA plates for 12 hours. Bacterial numbers were counted and represent the number of the bacteria in whole lung samples. This mode of infection more accurately evaluates mucociliary clearance than other pulmonary infection models, such as intratracheal infection. See Teichgräber et. al., "Ceramide Accumulation Mediate Inflammation, Cell Death And Infection Susceptibility In Cystic Fibrosis," *Nat Med.* 14(4):382-391 (2008); Zhang et. al., "Kinase Suppressor Of Ras-1 Protects Against Pulmonary *Pseudomonas aeruginosa* Infections," *Nat Med.* 17(3): 341-346 (2011), which are hereby incorporated by reference in their entirety.

Example 6

Statistics

Data are expressed as arithmetic means±SD and performed statistical analysis as indicated. Since all values were normally distributed, one-way ANOVA was applied. Significances are indicated in the figures with asterisks.

Example 7

Confocal Microscopy and Discussion

Samples were examined with a Leica TCS-SP5 confocal microscope equipped with a 100× oil emersion lens, and images were analyzed with Leica LCS software (Leica Microsystems). All comparative samples were measured with identical settings.

Ceramide is increased in the lungs of CF subjects and mice (FIG. 1A), and is an important factor in the susceptibility of CF mice to *P. aeruginosa* infection. See Grassmé et. al., "CFTR-dependent Susceptibility Of The Cystic Fibrosis-Host To *Pseudomonas aeruginosa*," *Int J Med Microbiol.* 300(8):578-83 (2010), which is hereby incorporated by reference in its entirety. Previous studies demonstrated that pharmacological inhibition of acid sphingomyelinase or genetic heterozygosity of the acid sphingomyelinase gene are sufficient to normalize ceramide levels in mouse CF lungs. See Becker et. al., "Acid Sphingomyelinase Inhibitors Normalize Pulmonary Ceramide And Inflammation In Cystic Fibrosis," *Am J Respir Cell Mol Biol.* 42(6):716-24 (2010), which is hereby incorporated by reference in its entirety.

In addition, $CF^{MHH}$Cftr-deficient mice inhaled acid ceramidase, which hydrolyzes ceramide. This inhalation corrected ceramide levels in the bronchial epithelial cells of CF mice (FIG. 1B). Inhalation of the solvent, i.e., 0.9% NaCl did not affect ceramide levels.

Figure 2:
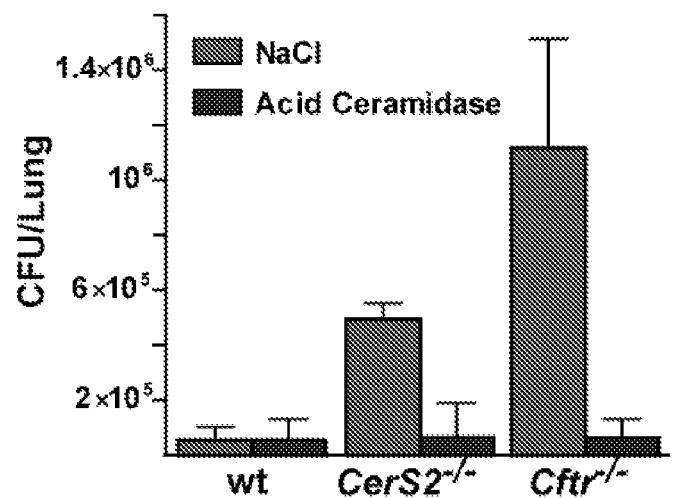
FIG. 2 demonstrates that recombinant acid ceramidase prevents *P. aeruginosa* infection in the lungs of mice accumulating ceramide. Two mouse models were used. One (CerS2−/−) is a genetic knockout for a ceramide producing enzyme, ceramide synthase 2. Another (Cftr−/−) has a mutation in the Cystic Fibrosis transmembrane protein gene and are a model of Cystic Fibrosis. The wild type, CerS2−/− or Cftr−/− mice either received a single inhalation of saline (light grey) or acid ceramidase (dark grey), and then were infected with *P. aeruginosa*. Two hours later they were sacrificed and the titer of *P. aeruginosa* remaining in the mouse lungs was determined.

In another example, Cftr−/−, CerS2 or normal mice were inhaled with saline or acid ceramidase and then infected with *P. aeruginosa* (FIG. 2). $CF^{MHH}$Cftr-deficient and CerS2 mice accumulate ceramide in their lungs relative to normal mice. Two hours after inhalation they were sacrificed and the remaining bacteria in the lungs was quantified. Wild-type mice cleared the *P. aeruginosa* effectively, whereas Cftr−/− or CerS2−/− mice inhaled with saline could not and had large numbers of remaining bacteria. In contrast, Cftr−/− or CerS2−/− mice inhaled with acid ceramidase had very low bacterial titers like normal mice.

The identification of irregularities in naive CF airways provides a novel concept for the prevention of infection in CF subjects. The present examples provide for several approaches to thwarting infection and treating the leading cause of death for subjects with CF.

Example 8

AC Inhalation Protects Against *Pseudomonas* Infections

Mice were inhaled with 100 micrograms of recombinant acid ceramidase (AC) in 0.8 mL of 0.9% NaCl 30 to 45 minutes before intranasal infection with $1\times10^8$ colony-forming units (CFU) of *P. aeruginosa* strain 762 or ATCC 27853. The lungs were removed 4 hours after infection, homogenized, lysed in 5 mg/mL saponin for 10 minutes, and washed. Aliquots were plated on LB plates and allowed to grow overnight. CFUs on the LB plates were counted to determine the number of *P. aeruginosa* bacteria in the lung. Shown are means±standard deviation of four independent experiments.

Figure 3:
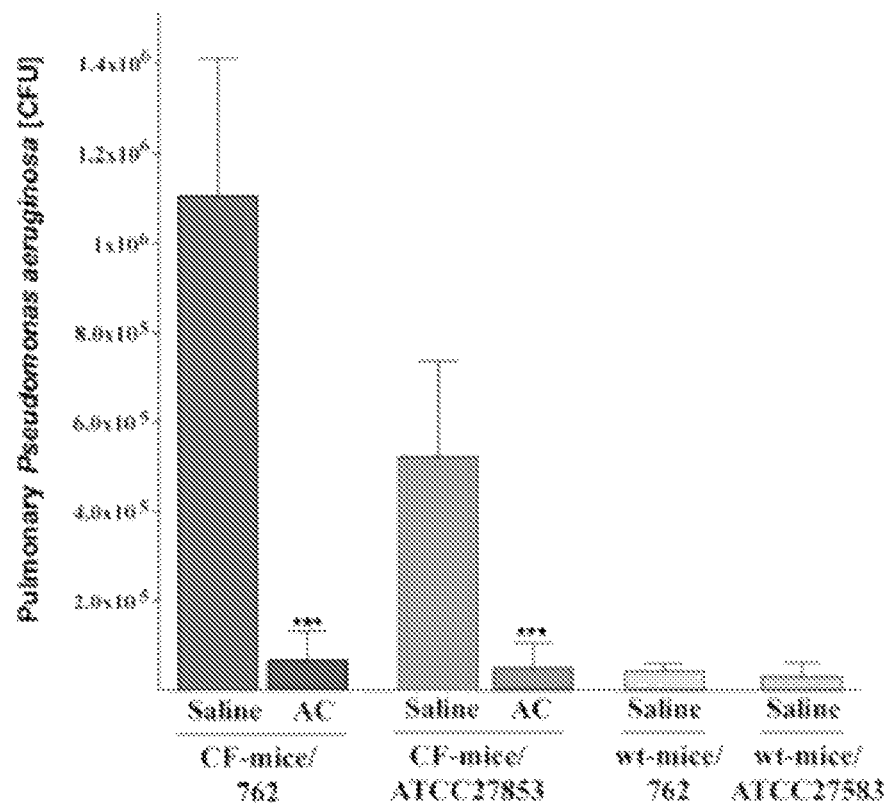
FIG. 3 shows results of mice that inhaled 100 µg AC in 0.8 mL of 0.9% NaCl 30 to 45 minutes before intranasal infection with $1\times10^8$ colony-forming units (CFU) of *P. aeruginosa* strain 762 or ATCC 27853. The lungs were removed 4 hours after infection, homogenized, lysed in 5 mg/mL saponin for 10 minutes, and washed. Aliquots were plated on LB plates and allowed to grow overnight. CFUs on the LB plates were counted to determine the number of *P. aeruginosa* bacteria in the lung. Shown are means±s.d. of four independent experiments.

A single inhalation of AC prevented infection of CF mice with two different strains of *P. aeruginosa* (FIG. 3). Clinical strain 762 was originally obtained from a urinary tract infection, while strain ATCC 27853 is a laboratory strain. Inhalation of saline alone was used as a control.

CF mice were inhaled with recombinant acid ceramidase (100 micrograms in 0.8 mL of 0.9% NaCl). Saline was used as a control. In all cases, mice were inhaled 30-45 minutes before inhalation with clinical *Pseudomonas aeruginosa* strain 762, and then sacrificed 4 hours after. The lungs were removed 4 hours after infection, homogenized, lysed in 5 mg/mL saponin for 10 minutes, and washed. Aliquots were plated on LB plates and allowed to grow overnight. CFUs on the LB plates were counted to determine the number of *P. aeruginosa* bacteria in the lung.

Inhalation of CF mice with recombinant acid ceramidase prevented infection with clinical strain 762 *P. aeruginosa* to a similar degree (FIG. 3).

Although preferred embodiments have been depicted and described in detail herein, it will be apparent to those skilled in the relevant art that various modifications, additions, substitutions, and the like can be made without departing from the spirit of the invention and these are, therefore, considered to be within the scope of the invention as defined in the claims which follow.

What is claimed:

1. A method for improving pathogenic clearance in a subject having Cystic Fibrosis, COPD, and/or an open wound, said method comprising:
    selecting a subject having Cystic Fibrosis, COPD, and/or an open wound and
    administering to said selected subject a therapeutically effective amount of ceramidase under conditions effective to reduce ceramide and improve pathogenic clearance of a *Pseudomonas* pathogen in said selected subject.

2. The method of claim 1, wherein the subject is selected based on elevated ceramide levels compared to a reference level for a subject not having said Cystic Fibrosis, COPD, and/or an open wound.

3. The method of claim 1, wherein said selecting is based on ceramide level in lung epithelium, nasal epithelium, mucus, and/or cells isolated from an open wound site.

4. The method of claim 1, wherein said administering is carried out under conditions effective to normalize ceramide levels in the subjects' respiratory epithelia, mucus, or cells at an open wound site.

5. The method of claim 1, wherein said ceramidase is acid ceramidase.

6. The method of claim 1, wherein one or more additional agents that reduce ceramide levels are administered in combination with said ceramidase.

7. The method of claim 6, wherein said one or more additional agents are selected from the group consisting of one or more additional ceramide reducing agents, one or more acid sphingomyelinase inhibitors, one or more agents to reduce infection, and combinations thereof.

8. The method of claim 7, wherein said one or more additional agents is one or more agents to reduce infection and is selected from the group consisting of antibiotics, reagents that block binding of pathogens to lung epithelium, reagents to reduce mucus viscosity, chaperone reagents to enhance missing protein function, and combinations thereof.

9. The method of claim 7, wherein said ceramidase is administered simultaneously, separately, or sequentially with said one or more additional agents.

10. The method of claim 1, wherein said administering is oral, topical, intranasal, intraperitoneal, intravenous, subcutaneous, or by aerosol inhalation.

11. The method of claim 10, wherein said administering is by aerosol inhalation.

12. The method of claim 1, wherein the ceramidase is administered in an amount from 0.001 mg/kg to 500 mg/kg.

13. The method of claim 1, wherein said *Pseudomonas* pathogen is *Pseudomonas aeruginosa*.

14. The method of claim 1, wherein said ceramidase is administered prior to onset of infection.

15. The method of claim 1, wherein said ceramidase is administered after onset of infection.

16. The method of claim 1, wherein the selected subject has Cystic Fibrosis.

17. The method of claim 1, wherein the selected subject has COPD.

18. The method of claim 1, wherein the selected subject has an open wound.

* * * * *